United States Patent
Patek et al.

(10) Patent No.: US 11,823,783 B2
(45) Date of Patent: Nov. 21, 2023

(54) DYNAMIC EQUIVALENT ON BOARD ESTIMATOR

(71) Applicant: DexCom, Inc., San Diego, CA (US)

(72) Inventors: Stephen D. Patek, Charlottesville, VA (US); Enrique Campos-Náñez, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 59 days.

(21) Appl. No.: 16/907,037

(22) Filed: Jun. 19, 2020

(65) Prior Publication Data
US 2020/0402634 A1 Dec. 24, 2020

Related U.S. Application Data

(63) Continuation of application No. 16/906,812, filed on Jun. 19, 2020.
(Continued)

(51) Int. Cl.
| | |
|---|---|
| *G16H 20/17* | (2018.01) |
| *G06N 5/04* | (2023.01) |
| *G16H 20/30* | (2018.01) |
| *G16H 40/67* | (2018.01) |
| *G16H 50/50* | (2018.01) |
| *G16H 10/60* | (2018.01) |

(Continued)

(52) U.S. Cl.
CPC ............ *G16H 20/17* (2018.01); *G06N 5/04* (2013.01); *G16H 10/60* (2018.01); *G16H 20/30* (2018.01); *G16H 20/60* (2018.01); *G16H 40/67* (2018.01); *G16H 50/20* (2018.01); *G16H 50/30* (2018.01); *G16H 50/50* (2018.01); *G16H 50/70* (2018.01)

(58) Field of Classification Search
CPC ........ G16H 20/17; G16H 10/60; G16H 20/30; G16H 20/60; G16H 40/67; G16H 50/20; G16H 50/30; G16H 50/50; G16H 50/70; G06N 5/04
See application file for complete search history.

(56) References Cited

U.S. PATENT DOCUMENTS

| | | | |
|---|---|---|---|
| 11,241,536 B2 * | 2/2022 | Yang | A61M 5/1723 |
| 2011/0021898 A1 * | 1/2011 | Wei | G06F 16/285 |
| | | | 600/365 |

(Continued)

FOREIGN PATENT DOCUMENTS

WO 2016201120 A1 12/2016

OTHER PUBLICATIONS

Dalla Man et al., "Meal Simulation Model of the Glucose-Insulin System", IEEE Trans Biomed Engineering (2007) 54(10):1740-1749.
(Continued)

*Primary Examiner* — Eliza A Lam
(74) *Attorney, Agent, or Firm* — Kaplan Breyer Schwarz, LLP; Stuart H. Mayer

(57) ABSTRACT

Adaptive on board estimation of exogenous pharmacon responsive to transient (i.e., impermanent) physiological effects is provided. Dynamically estimating an equivalent amount of an exogenous pharmacon on board (XOB), such as insulin and/or carbohydrates, left in the subject, is based on predictions of glucose time-series data. These estimated values, such as insulin on board (IOB), are useful for diabetes management software, including decision support and/or artificial pancreas (AP) algorithms, for example.

25 Claims, 14 Drawing Sheets

Related U.S. Application Data

(60) Provisional application No. 62/863,648, filed on Jun. 19, 2019.

(51) Int. Cl.
*G16H 50/30* (2018.01)
*G16H 50/70* (2018.01)
*G16H 50/20* (2018.01)
*G16H 20/60* (2018.01)

(56) References Cited

U.S. PATENT DOCUMENTS

| | | | |
|---|---|---|---|
| 2014/0066886 A1* | 3/2014 | Roy | A61B 5/14532 604/504 |
| 2014/0066892 A1* | 3/2014 | Keenan | G16H 10/40 604/506 |
| 2017/0182248 A1 | 6/2017 | Rosinko | |

OTHER PUBLICATIONS

Hughes et al., "Anticipating the next meal using meal behavioral profiles: A hybrid model-based stochastic predictive control algorith for T1DM", Comput Methods Programs Biomed. (2011) 102(2):138-148.

"Understanding Insulin On Board (IOB)," Alberta Diabetes Link, 2016, 1 page, Retrieved from the Internet: URL: https://albertadiabeteslink.ca/process.php?docname=Understanding-Insulin-on-Board-2016-1.pdf.

Roppenheimer: "Understanding the AndroidAPS Screens," 17 Sep. 2018, [Retrieved on May 9, 2023], XP093045426, 10 pages, Retrieved from the Internet: URL: https://github.com/roppenheimer/AndroidAPS-alt-Guide/blob/9685cf7b6e97ba5609f85fbab4fc43702414adfb/docs/pages/Screenshots.md.

* cited by examiner

DYNAMIC EQUIVALENT ON BOARD ESTIMATOR

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/906,812, filed Jun. 19, 2020, which claims the benefit of priority to U.S. Provisional Application No. 62/863,648, filed on Jun. 19, 2019. Each of the aforementioned applications is incorporated by reference herein in its entirety, and each is hereby expressly made a part of this specification.

BACKGROUND

Within diabetes management systems, known on board amounts of various exogenous pharmacons are important for improving diabetes management software. Unfortunately, the concentration or mass of these pharmacons are difficult to accurately determine in real-time, at least partly because measuring the state of absorption and distribution of exogenous pharmacons is impractical in vivo (as opposed to continuous glucose monitoring (CGM)). To address this problem, prior art techniques rely on reporting of ingestion and/or injection of the pharmacon along with an assumed and fixed time-action curve to extrapolate the quantity of the pharmacon present in the metabolism at a later time (exogenous pharmacon on board (XOB)). However, the human metabolism is highly complex, varying from subject to subject and from day to day, and often not following predefined action curves.

SUMMARY

Adaptive on board estimation of exogenous pharmacon responsive to transient (impermanent) physiological effects is provided. Dynamically estimating an equivalent amount of an exogenous pharmacon on board (XOB), such as insulin and/or carbohydrates, left in the subject, is based on predictions of glucose time-series data. These estimated values, such as insulin on board (JOB), are useful for diabetes management software, including decision support and/or artificial pancreas (AP) algorithms, for example.

In an embodiment, a system comprises an input compiler configured to receive and process input data; an exogenous pharmacon on board (XOB) estimator; and an output compiler.

In some embodiments, the input data corresponds to glucose concentration readings provided by a continuous glucose monitoring (CGM) system, insulin injection/infusion data, data on ingested meals, glucagon or other pharmacon dose and/or injection data, exercise data, or stress data. Alternatively or additionally, the input data comprises data pertaining to insulin, and/or the input data comprises data pertaining to carbohydrates.

Some embodiments further comprise a continuous glucose monitoring (CGM) system in communication with the input compiler and configured to provide the input data to the input compiler. Alternatively or additionally, a closed-loop delivery system is provided in communication with the input compiler and configured to provide the input data to the input compiler. In some embodiments, the input data comprises a sequence of insulin dose recommendations or glucagon dose recommendations.

In some embodiments, the input compiler is configured to compile at least one of (1) data related to a pharmacon whose glucose-effect equivalent is being compiled or (2) data related to the relevant history of continuous glucose monitoring (CGM) system readings.

In some embodiments, the output compiler is an XOB output compiler configured to render an XOB estimation. The XOB estimation may comprise an insulin on board (JOB) estimation and/or a carbohydrates on board (COB) estimation.

In some embodiments, the XOB estimator is configured to estimate the glucose equivalent effect of the pharmacon at a predetermined time. Alternatively or additionally, the XOB estimator comprises a baseline time-series estimator, an iterative time-series comparator, and a time-series comparator. The baseline time-series estimator may be a stateless machine that receives historical XOB amounts and continuous glucose monitoring (CGM) system history and produces a time-series that approximates future values of glucose. The iterative time-series comparator is configured to combine a procedure that generates candidate XOB amounts with a modification of the time-series estimator in which historical XOB amounts are substituted with the XOB amount under consideration. The time-series comparator is configured to match a pair of time-series that can be any measure of distance or similarity between the series.

In an embodiment, a method comprises receiving exogenous pharmacon data for a time T1, and glucose time-series data for a time period preceding a time T2 of on board estimation of the pharmacon; estimating baseline glucose time-series data from the time T2 of XOB estimation into a time T3 based on the data for time T1 and continuous glucose monitoring (CGM) system data for the time period preceding T2; iteratively estimating a plurality of glucose time-series data from the time T2 to the time T3 based on a range of possible values for the data at the time T2 and the CGM data for the time period preceding T2; comparing the baseline glucose time-series data with the plurality of glucose time-series to determine a best match from which an exogenous pharmacon on board (XOB) estimate is selected; and outputting the XOB estimate.

In some embodiments, the exogenous pharmacon data is received from one of a subject or a connected device. Alternatively or additionally, the exogenous pharmacon data comprises insulin on board (JOB), and/or the connected device is an insulin pump. Alternatively or additionally, the exogenous pharmacon data comprises carbohydrates on board (COB).

In some embodiments, the method further comprises removing at least one of non-reliable data or spurious data from the exogenous pharmacon data and the glucose time-series data. At least one of the exogenous pharmacon data or the glucose time-series data comprises one or more of doses or amounts of previously injected or ingested pharmacon data. The glucose time-series data may be continuous or semi-continuous.

In some embodiments, the iteratively estimating ranges from the pharmacon being removed from 0 to the pharmacon having the full amount.

In some embodiments, outputting the XOB estimate comprises outputting the XOB estimate to at least one of a diabetes management system, a diabetes management algorithm, a user interface, a bolus calculator, or an artificial pancreas (AP) system.

In some embodiments, the XOB estimate comprises the equivalent amount of a pharmacon left in a subject. The pharmacon comprises at least one of insulin or carbohydrates.

In an embodiment, a system comprises an input compiler, wherein the input compiler receives and processes input data relating to a pharmacon; an exogenous pharmacon on board (XOB) estimator, wherein the XOB estimator uses estimation to account for transient changes in pharmacon absorption of the pharmacon, and wherein the XOB estimator determines an XOB estimation; and an output compiler, wherein the output compiler renders the XOB estimation.

In some embodiments, the transient changes in pharmacon absorption are determined by data from a continuous glucose monitoring (CGM) system. The XOB estimation may comprise an insulin on board (JOB) estimation and/or a carbohydrates on board (COB) estimation. The pharmacon may be insulin and/or carbohydrates.

In some embodiments, the input data corresponds to glucose concentration readings provided by a continuous glucose monitoring (CGM) system, insulin injection/infusion data, data on ingested meals, glucagon or other pharmacon dose and/or injection data, exercise data, or stress data. The input data may comprise data pertaining to insulin and/or data pertaining to carbohydrates.

In some embodiments, the system further comprises a continuous glucose monitoring (CGM) system in communication with the input compiler and configured to provide the input data to the input compiler. Alternatively or additionally, the system further comprises a closed-loop delivery system in communication with the input compiler and configured to provide the input data to the input compiler. The input data may comprise a sequence of insulin dose recommendations or glucagon dose recommendations.

In some embodiments, the input compiler is configured to compile at least one of (1) data related to a pharmacon whose glucose-effect equivalent is being compiled or (2) data related to the relevant history of continuous glucose monitoring (CGM) system readings.

In some embodiments, the XOB estimator is configured to estimate the glucose equivalent effect of the pharmacon at a predetermined time. The XOB estimator may comprise a baseline time-series estimator, an iterative time-series comparator, and a time-series comparator. The baseline time-series estimator may be a stateless machine that receives historical XOB amounts and continuous glucose monitoring (CGM) system history and produces a time-series that approximates future values of glucose. The iterative time-series comparator may be configured to combine a procedure that generates candidate XOB amounts with a modification of the time-series estimator in which historical XOB amounts are substituted with the XOB amount under consideration. The time-series comparator may be configured to match a pair of time-series that can be any measure of distance or similarity between the series.

In an embodiment, a method comprises receiving insulin data for a time T1, and continuous glucose monitoring (CGM) system time-series data for a time period preceding a time T2 of insulin on board (JOB) estimation; estimating baseline glucose time-series data from the time T2 of IOB estimation into a time T3 based on the insulin data for time T1 and CGM system data for the time period preceding T2; iteratively estimating a plurality of glucose time-series data from the time T2 to the time T3 based on a range of possible values for the insulin data at the time T2 and the CGM data for the time period preceding T2; comparing the baseline glucose time-series data with the plurality of glucose time-series to determine a best match from which an IOB estimate is selected; and outputting the IOB estimate.

In some embodiments, the insulin data is received from one of a subject or a connected device. The connected device may be an insulin pump.

In some embodiments, the method further comprises removing at least one of non-reliable data or spurious data from the insulin data and the CGM system time-series data. At least one of the insulin data or the CGM system time-series data comprises one or more of doses or amounts of previously injected or ingested insulin data. The CGM system time-series data may be continuous or semi-continuous.

In some embodiments, the iteratively estimating ranges from the insulin being removed from 0 to the insulin having the full amount.

In some embodiments, outputting the IOB estimate comprises outputting the IOB estimate to at least one of a diabetes management system, a diabetes management algorithm, a user interface, a bolus calculator, or an artificial pancreas (AP) system. The IOB estimate may comprise the equivalent amount of insulin left in a subject.

In an embodiment, a method comprises receiving carbohydrate data for a time T1, and continuous glucose monitoring (CGM) system time-series data for a time period preceding a time T2 of carbohydrates on board (COB) estimation; estimating baseline glucose time-series data from the time T2 of COB estimation into a time T3 based on the carbohydrate data for time T1 and CGM system data for the time period preceding T2; iteratively estimating a plurality of glucose time-series data from the time T2 to the time T3 based on a range of possible values for the carbohydrate data at the time T2 and the CGM data for the time period preceding T2; comparing the baseline glucose time-series data with the plurality of glucose time-series to determine a best match from which a COB estimate is selected; and outputting the COB estimate.

In some embodiments, the carbohydrate data is received from one of a subject or a connected device. The connected device may be a glucose monitor.

In some embodiments, the method further comprises removing at least one of non-reliable data or spurious data from the carbohydrate data and the CGM system time-series data. At least one of the carbohydrate data or the CGM system time-series data comprises one or more of doses or amounts of previously injected or ingested carbohydrate data. The CGM system time-series data may be continuous or semi-continuous.

In some embodiments, the iteratively estimating ranges from the carbohydrates being removed from 0 to the carbohydrates having the full amount.

In some embodiments, outputting the COB estimate comprises outputting the COB estimate to at least one of a diabetes management system, a diabetes management algorithm, a user interface, a bolus calculator, or an artificial pancreas (AP) system. The COB estimate may comprise the equivalent amount of carbohydrate left in a subject.

In an embodiment, a system comprises an automated insulin delivery (AID) algorithm configured to receive an estimate of a glucose concentration of a patient; and an insulin on board (JOB) estimator configured to provide an IOB estimate to the AID algorithm.

In some embodiments, the AID algorithm is comprised within a computing device. Alternatively or additionally, the AID algorithm comprises a semi closed-loop algorithm, a closed-loop algorithm, or an algorithmic recommendation system. The AID algorithm may be further configured to receive an updated estimate of the glucose concentration of the patient at predetermined intervals of time.

In some embodiments, the estimate of the glucose concentration of the patient is received as a continuous glucose monitoring (CGM) reading from a CGM sensor.

In some embodiments, the AID algorithm is configured to compute a desired insulin dose using the estimate of the glucose concentration of the patient. Alternatively or additionally, the AID algorithm is further configured to subtract the IOB estimate from the desired insulin dose to compute a bolus recommendation. Alternatively or additionally, the AID algorithm is further configured to provide the bolus recommendation to an insulin pump for delivering insulin to the patient.

In an embodiment, a method comprises receiving an estimate of a glucose concentration of a patient; receiving an insulin on board (JOB) estimate; computing a desired insulin dose using the estimate of the glucose concentration of the patient; and subtracting the IOB estimate from the desired insulin dose to compute a bolus recommendation.

In some embodiments, the method further comprises providing the bolus recommendation to an insulin pump for delivering insulin to the patient.

In some embodiments, the method further comprises receiving an updated estimate of the glucose concentration of the patient at predetermined intervals of time.

In some embodiments, the estimate of the glucose concentration of the patient is received as a continuous glucose monitoring (CGM) reading from a CGM sensor.

In an embodiment, a system comprises a monitoring device configured to receive input data pertaining to a patient; a handheld computing device configured to receive the input data from the monitoring device; and an exogenous pharmacon on board (XOB) calculator configured to perform an XOB estimation using the input data.

In some embodiments, the XOB calculator is locally implemented on a computing device. Alternatively, the XOB calculator is locally implemented on a computing device.

In some embodiments, the monitoring device comprises an insulin pen. The insulin pen may be configured to provide additional input data to the handheld computing device, wherein the XOB calculator is configured to perform the XOB estimation using the input data and the additional input data.

In some embodiments, the XOB calculator is further configured to render the XOB estimation via a display of the handheld computing device.

In some embodiments, the system further comprises an insulin pump configured to receive data from the handheld computing device and provide an amount of insulin to the patient based on the data received from the handheld computing device.

In some embodiments, the system further comprises an insulin pump configured to receive data from the handheld computing device and provide an amount of insulin to the patient based on the data received from the handheld computing device. Alternatively or additionally, the input data comprises data pertaining to insulin and/or the input data comprises data pertaining to carbohydrates.

In some embodiments, the XOB estimation comprises an insulin on board (IOB) estimation, and/or the XOB estimation comprises an insulin on board (IOB) estimation.

In some embodiments, the input data comprises a sequence of insulin dose recommendations or glucagon dose recommendations.

In some embodiments, the XOB calculator comprises an XOB estimator. The XOB estimator may be configured to estimate a glucose equivalent effect of a pharmacon at a predetermined time.

In some embodiments, the XOB estimator comprises a baseline time-series estimator, an iterative time-series comparator, and a time-series comparator. The baseline time-series estimator may be a stateless machine that receives historical XOB amounts and continuous glucose monitoring (CGM) system history and produces a time-series that approximates future values of glucose. The iterative time-series comparator may be configured to combine a procedure that generates candidate XOB amounts with a modification of the time-series estimator in which historical XOB amounts are substituted with the XOB amount under consideration. The time-series comparator may be configured to match a pair of time-series that can be any measure of distance or similarity between the series.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
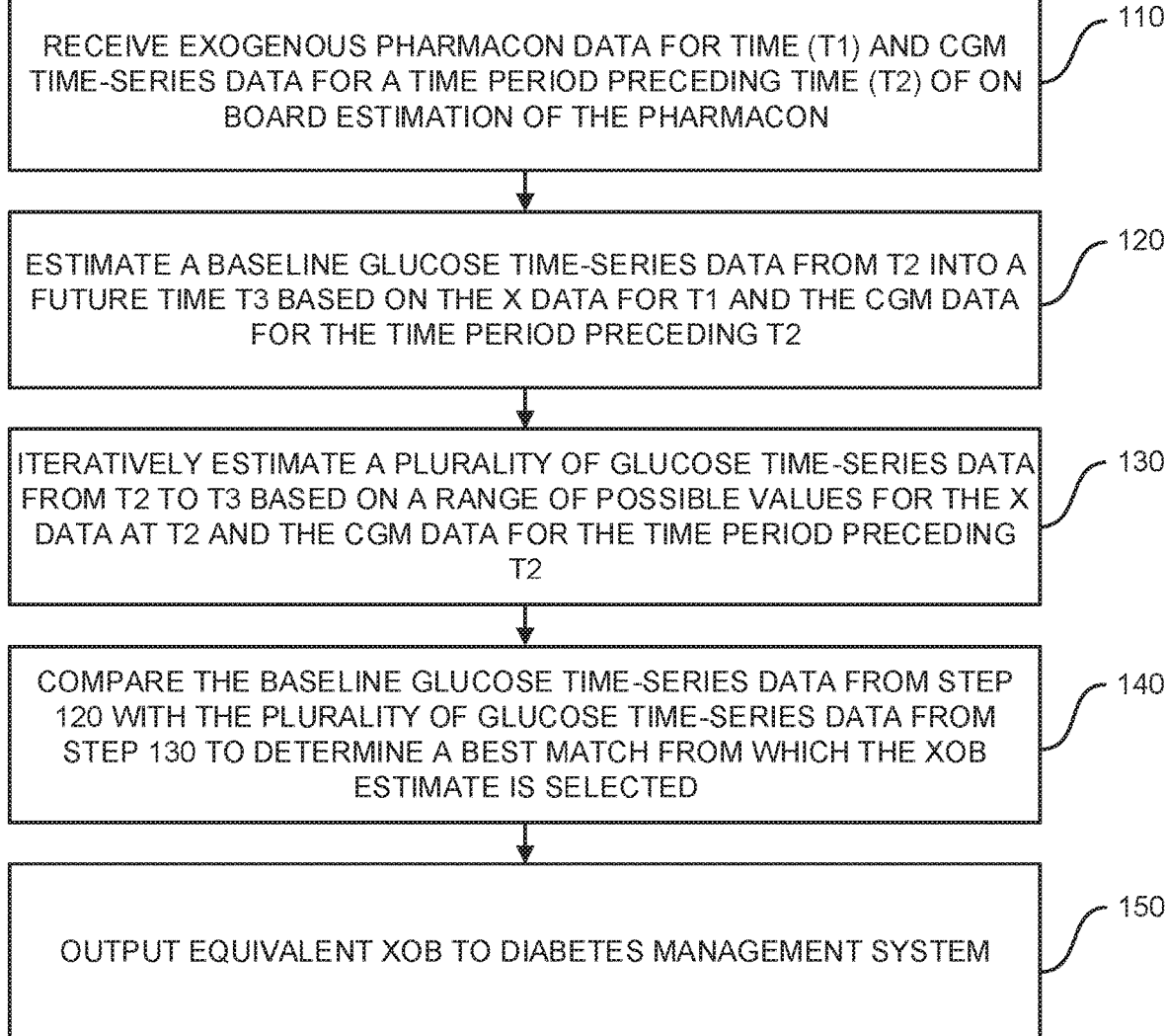
FIG. 1 is a flow diagram illustrating a method for determining the remaining effective amount of a previously injected or ingested pharmacon (exogenous pharmacon on board (XOB)) at estimation time.

The claimed subject matter is described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A pharmacon on board estimate is calculated using the principle of glucose-effect equivalence. According to this principle, the best on board estimate of a particular pharmacon at the current time is the amount of that pharmacon which will produce the closest glucose response to the predicted response due to historical (previous) pharmacon administrations. The estimate of one or more exogenous pharmacons in a subject is informed by available glucose data from the recent past and predicted future glucose time-series data and as such it is specific to the subject. Whenever possible, the XOB estimate also utilizes known (reported or estimated) data for other pharmacons to improve the accuracy of the estimate. This may involve for example, using carbohydrate data when estimating insulin. In other words, rather than extrapolating (e.g., solely) based on an exogenous pharmacon data from past reported pharmacon injection(s) and/or ingestion(s), the systems and methods described herein contemplate utilizing glucose time-series data and prediction methods to estimate equivalent XOB data at any requested time.

Figure 2:
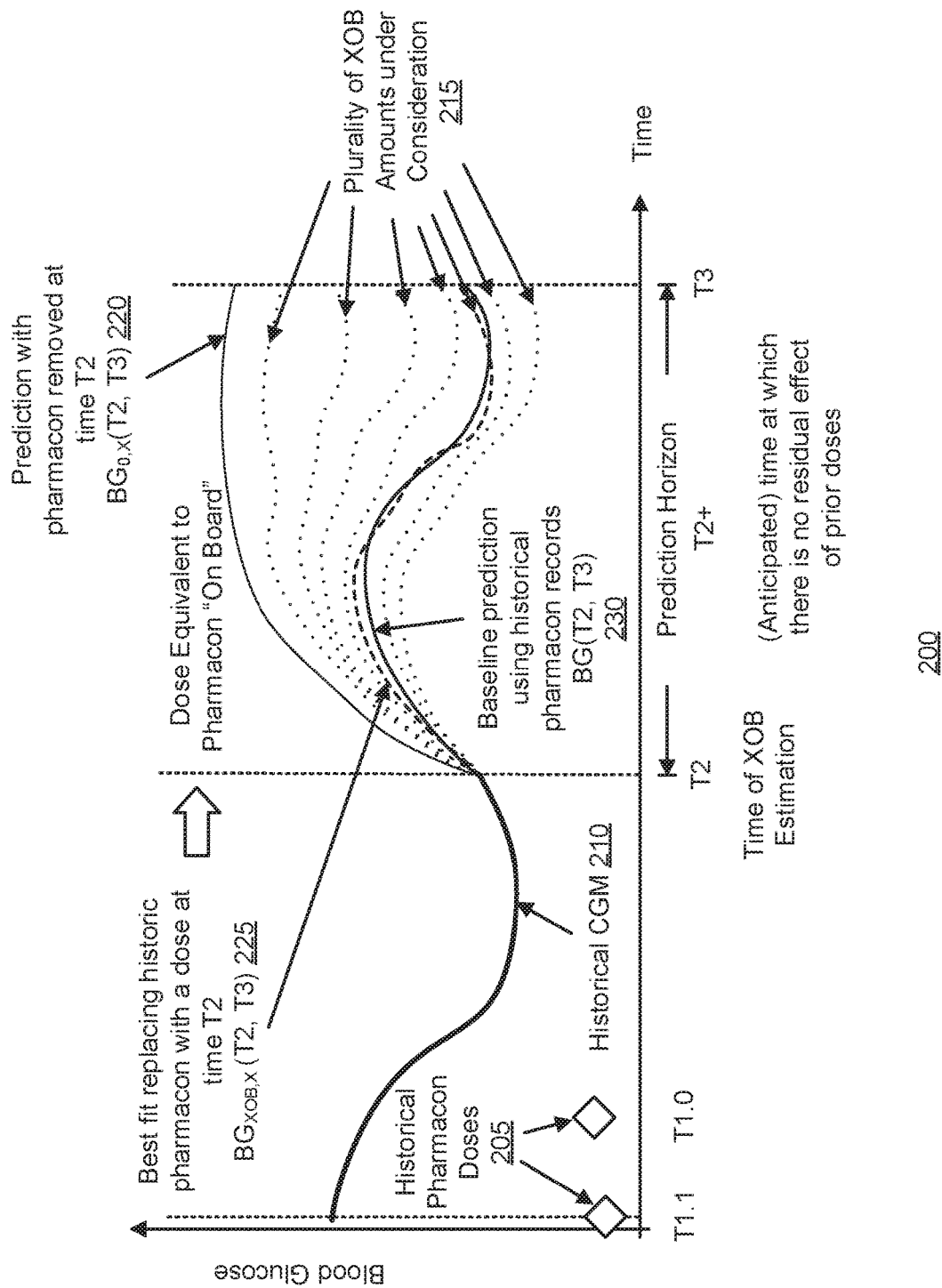
FIG. 2 is a graph illustrating the method of FIG. 1.
Figure 3A:
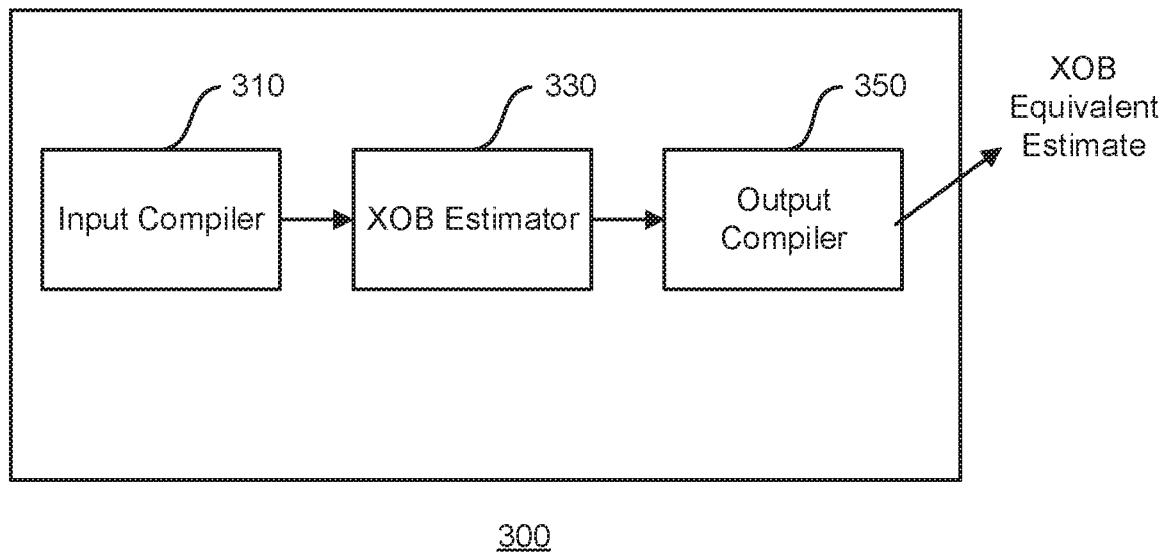
FIG. 3A is a block diagram of an example system in accordance with an embodiment.
Figure 3B:
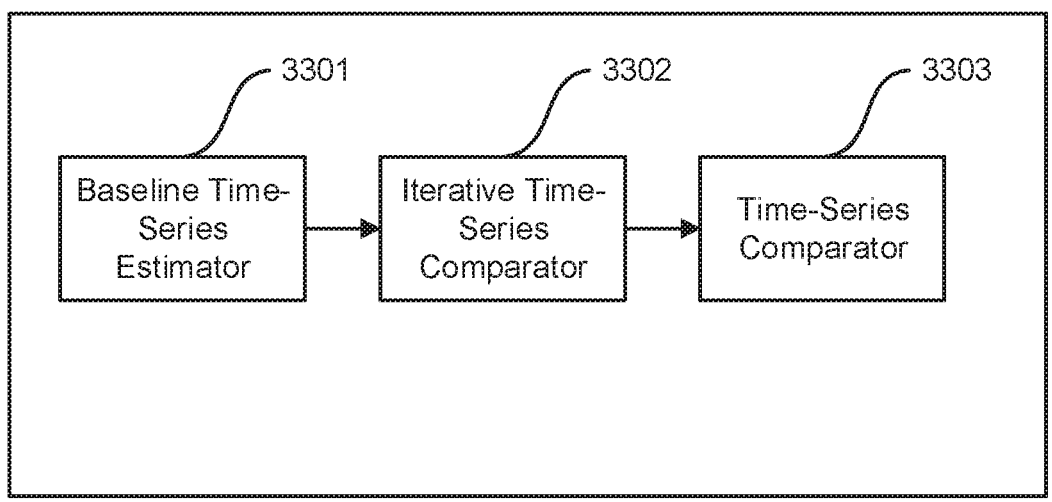
FIG. 3B is block diagram of an XOB estimator in an embodiment.

FIG. 1 is a flow diagram illustrating a method 100 for determining the remaining effective amount of a previously injected and/or ingested pharmacon (i.e., XOB) at estimation time. FIG. 2 is a graph 200 illustrating the method 100 of FIG. 1. FIG. 3A is a block diagram of an example system 300 in accordance with an embodiment. FIG. 3B is block diagram of an XOB estimator 330 in an embodiment.

For XOB, "X" represents an exogenous pharmacon that is ingested or injected and whose metabolism may be transiently affected by daily events including illness, stress, strenuous activity, and/or other transient physiological effects. Thus, exogenous pharmacon as used herein refers to a biologically active substance useful for the treatment of diabetes that is ingested and/or injected by a patient, the metabolism of which may be transiently affected by daily events including illness, stress, and other transient physiological effects. As used herein, the term "transient" means impermanent, and transient effects (or transient physiological effects) are those effects are those changes of a patient's pharmacon absorption during a time period, such as a time period of less than 48 hours, less than 36 hours, less than 24 hours, or less than 12 hours, etc., for example, depending on the implementation. While these are examples of daily events that cause transient effects on the metabolism of a subject, in general, any compound that has a bearing on the CGM/glucose time-series (the sensed variable) with a pharmacokinetic (or pharmacodynamic) property can be similarly calculated in accordance with the systems and methods described herein. Examples of exogenous pharmacons that are used in diabetes control include insulin, carbohydrates, glucagon, metformin, glucagon-like peptide-1 (GLP-1), and other Type I or II glucose control medications.

Because the amount of active pharmacon in the body cannot be directly measured, the systems and methods described herein provide an estimate of the remaining effective amount based on reported prior pharmacon administrations and recent glucose measurements. Examples of pharmacon records include self-reported pharmacon administration (provided by the patient, also referred to herein as the subject), automated pharmacon administration records (as provided by a connected device), or estimated pharmacon administrations provided by some other mechanism. Glucose measurements can be provided by a real-time CGM system, direct intravenous measurements, or a blood glucose monitor system (BGM), or by some other estimation procedure that reconstructs a glucose trace from BGM.

The systems and methods described herein determine a real-time estimate of the on board pharmacon (what is left in the body) based on the principle of glucose-effect equivalence. More specifically, the glucose-effect equivalent dose is defined as the pharmacon amount that is the closest replacement of previously administered pharmacon doses in terms of predicted glucose concentration effect.

Techniques provided herein use the history of glucose measurements to estimate transient metabolic influences and ultimately produce a glucose concentration prediction that reflects these estimates. In other words, systems and methods described herein provide how much action is really left at the time of estimation of on board equivalent based on what the glucose time-series estimations are, which may be different from the pre-defined action curves of the prior art because the systems and methods described herein take into account transient influences on the metabolism that cannot be predefined.

While useful as a real-time estimator, XOB calculations could be used retrospectively for pharmacon dose optimization, titrations, run-to-run optimization, and other similar adjustment algorithms.

At 110, exogenous pharmacon data is received for a time T1, and glucose time-series data is received for a time period preceding a time T2 of on board estimation of the pharmacon. The data may include one or more doses and/or amounts of previously injected and/or ingested pharmacon data. When multiple doses are received, the pharmacon data may be compiled or remain distinct for further processing.

Reports may be self-reported acknowledgements (generated by the user (i.e., the patient or subject)), automated reports generated by a connected device, or estimated via some other method. For example, when estimating insulin on board, a bolus can be self-reported or communicated by an insulin pump.

The data may be received and processed by an input compiler 310. The input compiler 310 may receive raw data and process it to remove non-reliable data and/or spurious data. Examples of approaches that may be used include interpolation and extrapolation of time-series CGM data, and removal of duplicate readings and calibration artifacts in the CGM time-series.

The glucose time-series are typically obtained by a real-time CGM system, but can also be direct intravenous measurements, or a BGM system, or by some other estimation procedure that reconstructs a glucose trace from BGM. In some implementations, measurement frequency is at least every fifteen minutes, such as every five minutes, for example. Glucose time-series data may be received in real time directly from a CGM device, or can be downloaded in bulk at the time of a request from an external source such as a data center by a wired or wireless connection. Glucose time-series data may be raw or processed and shall at least encompass times T1 through T2 but may include a longer time window.

At 120, baseline glucose time-series data is estimated from time T2 of XOB estimation into a future time T3 based on the X data for time T1 and the CGM data for the time period preceding T2.

The time-series estimator 320 may be used to perform the estimation. Estimation of future glucose time-series data may be provided by many known methods of prediction, but generally uses continuous or semi-continuous glucose time-series data. Any black-box estimate of future glucose time-series based on past CGM data, which is influenced by the transient physiological effects, may be used herein. Estimation of future glucose time-series data may also be informed by data from one or more previous injection(s) and/or ingestion(s) of the exogenous pharmacon (being estimated), to the extent the pharmacon may have ongoing action in the body at time T2. This operation assumes trustworthiness of the reported pharmacon.

While not required, in some embodiments, estimation of future glucose time-series data is based on a mathematical model that represents the subject's glucose response to the pharmacon being estimated. For example, a model of insulin-carbohydrate-glucose may be used to explain the effect of an insulin bolus on glucose control, the structure and/or parameters of which may be tuned to that subject's physiological characteristics.

While not required, estimation of future glucose time-series data can use hybrid approaches which, in addition to a mathematical model, uses subject-specific estimates of transient metabolic variations such as exercise, stress, or illness, not explained by the mathematical model.

Estimates of metabolic variations may be based on a black-box model, analysis of historical data, and/or the use of additional data inputs. For example, exercise will produce temporary changes to insulin-sensitivity that may affect the glucose-effect of the pharmacon. Using a heart-rate signal from a monitor may be used to quantify this effect and thus the prediction.

Estimation of future glucose time-series data may also be informed by data from one or more other exogenous pharmacons (other than the pharmacon being estimated). For example, an IOB estimation may utilize carbohydrate data to the extent available based on reporting or estimation in the system.

At 130, a plurality of glucose time-series data from time T2 to time T3 is iteratively estimated based on a range of possible values for the X data at time T2 and the CGM data for the time period preceding T2.

The time-series estimator 320 may be used to perform the estimation. Because the exogenous pharmacon cannot be directly measured at the time T2 of the request for an on board calculation, some embodiments test a range of possible values for that pharmacon administered at time T2 as candidates to match the glucose-effect corresponding to the pharmacon from known reported administrations of the pharmacon at time(s) T1. A pharmacon amount is tested by using the time-series estimator but replacing the remaining pharmacon administered at time(s) T1 with the amount at time T2.

In some embodiments, the iterative estimation ranges from the pharmacon being removed from the model (X=0) to the pharmacon having the full amount (e.g., dosed at time T1). Alternatively, the range of possible values can start with zero (0 for X data at time T2) and incrementally go up to a smaller dose based on additional information regarding the pharmacokinetics.

At 140, the baseline glucose time-series data from 120 is compared with the plurality of glucose time-series from 130 to determine a best match from which the XOB estimate is selected. The comparison may be performed by the time-series comparator 330.

In other words, a pharmacon amount is designated as the pharmacon on board (XOB) or glucose-effect equivalent amount of pharmacon at time T2 if its corresponding glucose time-series data (from 130) provides the best match to the base time-series (from 120).

The match of a pair of time-series can be any measure of distance or similarity between the series. This may include multiple norms, Fourier series coefficients, auto-regressive properties of the series, dynamic time-warping, and/or edit distance, for example. It may also include other forms of categorization including clustering analysis, i.e., two time-series have a good match if they belong to the same cluster.

In one example, the best match is determined with a prediction computed at 130 that minimizes the total differences to the prediction computed at 120. Alternatively, the match could be defined by the difference in predicted glucose level at the end of the prediction horizon (e.g., time T3), or as a weighted sum of the differences between the two predictions. The weights used in the sum can represent a forgetting factor, so that the distance of the final point in the prediction horizon (e.g., time T3) has more weight than the distance at the beginning of the prediction horizon (e.g., time T2). These weights may also reflect trustworthiness of the prediction due to other exogenous factors.

At 150, the equivalent XOB is outputted to a diabetes management system, e.g., using the output compiler 340. The output compiler 340 may receive and send the XOB selected from the best match time-series data and/or the output compiler 340 may further process the XOB estimate to provide a graphical or functional output. The output compiler 340 may produce a dynamic graphical or functional output, when the XOB is continuously estimated, to provide a user or algorithm with a continuous estimate.

Alternatively or additionally, the equivalent amount of the pharmacon, e.g., insulin and/or carbohydrates, left in the subject may be outputted to one or more of a diabetes management algorithm, a user interface, a bolus calculator, or an AP system.

In some embodiments wherein the pharmacon is carbohydrates, the output may be also be provided to a meal-behavior estimation algorithm (e.g., "time since last meal" feature), prediction algorithms, recommendation engines, features into an individualized model of behavior (e.g., timing of meals, composition of meals, acknowledgement timing behavior, timing of diabetes technology interaction, etc.), linked to other behaviors such as physical activity/exercise, and carbohydrates on board value without need to announce carbohydrates, for example.

FIG. 2 is a graph 200 illustrating the method of FIG. 1. The x-axis represents time and the y-axis represents glucose concentration. The diamonds 205 represent pharmacon data such as historical pharmacon doses.

In FIG. 2, times T1.0 and T1.1 correspond to times of one or more historical pharmacon amounts or doses 205 reported or estimated from injection and/or ingestion of the pharmacon at time T1.X, which precede a request for estimation of pharmacon on board XOB equivalent value. Pharmacon amounts and/or doses 205 (identified at times T1.0, T1.1, etc.) are injection(s) and/or ingestion(s) that have not yet been fully metabolized and thus a fraction of which remains active in the body at the time of the XOB request T2.

Additionally or alternatively, equivalent XOB estimations calculated as a result of previous requests can be used for further XOB calculations when repeated requests occur over a time period of action of the pharmacon most recently estimated or reported. The doses or amounts (injected and/or ingested) can be reported or estimated as described in more detail herein.

Notably, although not illustrated here, additional times of other pharmacon injections/infusions at subsequent times T1.2, T1.3, . . . may be included, such as for example, when a subject has injected multiple micro-doses of insulin and/or continuous infusion from an insulin pump have been received.

Thus, the diamonds 205 represent historical pharmacon doses that have remaining effective concentrations at time T2. Notably, numerous other pharmacon doses may exist prior to time T1, but are not generally considered if there is no residual effect at time T2. Also notable is that more than one or two doses may have a residual effect at time T2 as may be appreciated by one skilled in the art.

In FIG. 2, time T2 corresponds to a time at which the XOB estimate is requested and/or calculated. Time T2, following the request or initiation of the XOB calculation, is also the approximate starting point for the estimation of future glucose time-series data (e.g., start of the prediction horizon). Time T2 is also typically the time of the last reading in the glucose time-series data used for the estimation/prediction.

The line 210 represents the CGM time-series data used in the estimation of future glucose time-series data. In general, glucose time-series data useful for the systems and methods described herein use CGM time-series data beginning at least at time T1; however, the data may include additional time-series data from time preceding T1 and/or other influence from data preceding time T1, such as filtering, smoothing, or tuning effects.

In FIG. 2, time T3 corresponds to an end of the estimation of future glucose time-series data, also referred to as the end of the prediction horizon, which is the length of the estimation made from time T2 to time T3. Preferably, the length of the prediction horizon is somewhere beyond the time T2+ at which there is no residual effect of prior pharmacon doses (the diamonds 205) used in the baseline estimation. This normally corresponds to the time the pharmacon doses have been fully metabolized, cleared, or absorbed by the body.

The line 230 represents the estimation of a baseline glucose time-series data from time T2 to time T3, sometimes referred to as the baseline prediction. The estimation is based on historical pharmacon doses (the diamonds 205) obtained for times T1.0, T1.1, etc. and the glucose time-series data (the line 210) for the time period preceding T2 as described further herein (e.g., at 120).

The lines 215 and 225 (dotted and dashed, respectively) represent two of the plurality of iterative estimations of future glucose time-series data from time T2 to time T3. The line 220 represents the estimation with the pharmacon removed at time T2 (zero remaining effective amount of pharmacon). The line 225 represents the best match glucose time-series estimation from 130 as compared to the baseline glucose time-series data from 120 as described in more detail at 140. The effect of historical doses (the diamonds 205) ends at an anticipated time T2+ that occurs before the end of the prediction horizon (time T3).

FIG. 3A is a block diagram of an example system 300 in accordance with an embodiment. The system 300 comprises an input compiler 310, an XOB estimator 330, and an output compiler 350.

In an implementation, the input compiler 310 is embodied as software that processes input data for processes described herein. The input data provided to, and received at, the input compiler 310 may correspond to glucose concentration readings most commonly provided by a CGM system, insulin injection/infusion data, data on ingested meals, glucagon or other pharmacon dose and/or injection data, exercise data, or stress data.

In a real-time embodiment, the input data may originate in sensors (e.g., CGM) connected to the input compiler 310 via Bluetooth, Wi-Fi, or any other communication protocol. Data may also be directly provided to the input compiler 310 from an application such as a closed-loop delivery system which generates a sequence of insulin dose recommendations or glucagon dose recommendations. In such an embodiment, both applications may coexist or conform a single software system. For retrospective applications, data and the input compiler may exist in a cloud service that aggregates and compiles data asynchronously.

As described with respect to 110, a purpose of the input compiler 310 is to compile data related to the pharmacon whose glucose-effect equivalent is being compiled, to compile and curate the relevant history of CGM system readings, and other data that may be used later in the process to improve the quality of the prediction.

The XOB estimator 330 may be referred to as a glucose effect equivalent estimator because it is the engine that estimates the glucose equivalent effect of the pharmacon at time T2. The XOB estimator 330 may be implemented as a library that can run local to the device where the user or algorithm (e.g., AP) requests an estimation, i.e., a smartphone, an insulin pump, or any other device generating the request. Alternatively, the algorithm can be implemented as an on-demand service, such as a cloud computing service. Such an embodiment may be useful in the case of retrospective analysis of data but could also be an alternative if the device issuing the request has limited memory/computation capacity.

The XOB output compiler 350 renders an XOB estimation into a form that is useful for the requesting entity (e.g., device, algorithm, patient, etc.). Examples of this include the following.

In an AP system implementation, the output from the output compiler 350 is an XOB estimate that is accessible through a software API. The output may contain information used to re-compute this estimate in a near future and speed up the computation. In an implementation, the output comprises an estimate of IOB. An AP system that does not require meal acknowledgments from the user may also request estimates of COB, when a meal was recently detected, in order to generate a meal bolus.

In a CGM/pen combination system implementation, the output from the output compiler 350 may be obtained by the requesting system via an API. An example of this system is a bolus calculator (e.g., see FIGS. 10A and 10B). In some implementations, the output comprises an estimate of IOB when computing a correction bolus, or COB when meal bolus calculation is requested at a later time than the meal.

In a cloud-based system implementation, the output compiler 350 may create, upon request, a data package containing the estimation. For example, the XOB estimate can be communicated back to the requesting application using JavaScript Object Notation (son).

A CGM real-time application implementation may display both IOB/COB information either statically (i.e., latest values of IOB/COB). This display can also be dynamic containing the recent history of both IOB/COB.

FIG. 3B is block diagram of the XOB estimator 330 in an embodiment, comprising a baseline time-series estimator 3301, an iterative time-series comparator 3302, and a time-series comparator 3303.

In an implementation, the baseline time-series estimator 3301 is a stateless machine that receives historical XOB amounts and CGM system history and produces a time-series that approximates the future values of glucose. It embodies the process described in 120 in either a local implementation of an estimator or a cloud services which receives the information described above and produces an estimate.

The algorithm implemented by the baseline time-series estimator 3301 can be any method relating historical XOB/CGM information to a glucose prediction. This includes the glucose predictors and may include other prediction approaches, e.g., prospective replay simulation.

The iterative time-series estimator 3302 combines a procedure that generates candidate XOB amounts with a modification of baseline time-series estimator 3301 in which historical XOB amounts are substituted with the XOB amount under consideration. Substituting historical XOB is understood as the procedure to zero-out amounts of XOB already distributed in the subject's body and delivering a new XOB dose at the time of the request. The procedure can be carried out by the algorithm using resources local to the device generating the request.

The time-series comparator 3303 may match a pair of time-series that can be any measure of distance or similarity between the series. This may include multiple norms, Fourier series coefficients, auto-regressive properties of the series, dynamic time-warping, and edit distance. It may also include other forms of categorization including clustering analysis, i.e., two time-series have a good match if they belong to the same cluster. In one example, the best match is determined with a prediction computed at 130 that minimizes the total differences to the prediction computed at 120.

Alternatively, the match could be defined by the difference in predicted glucose level at the end of the prediction horizon (time T3), or as a weighted sum of the differences between the two predictions. The weights used in the sum can represent a forgetting factor, so that the distance of the final point in the prediction horizon (time T3) has more weight than the distance at the beginning of the prediction horizon (time T2). These weights may also reflect trustworthiness of the prediction due to other exogenous factors.

For a person with diabetes, knowing the remaining amount of active insulin, or IOB, is often critical. Prior art IOB calculations typically use models for IOB that prorate current insulin values based on previous known insulin values (e.g., based on a reported insulin bolus delivered) and action curves that predefine how a body absorbs insulin. Most action curves are arbitrarily set by a system default and therefore not personalized to a particular subject. However whether using a system default or a personalized version of an action curve, absorption of insulin is subject to transient changes even within an individual due to factors such as stress, sickness, strenuous activity, etc. Because prior art IOB calculations are typically an assessment of remaining active insulin computed from insulin injections and/or infusions in the recent past, subjects and/or caregivers are required to set the duration of insulin action by choosing an insulin action curve, which typically occurs when a subject first configures a software application that computes IOB (in a pump or in an application). As a result, IOB estimates produced using prior art often inaccurately reflect remaining active insulin in the body. Accordingly, the systems and methods described herein estimate an equivalent insulin on board value that may be understood in terms of an insulin bolus theoretically required to achieve a similar glucose-clearing effect as that of insulin still active at the time of estimation.

Figure 4:
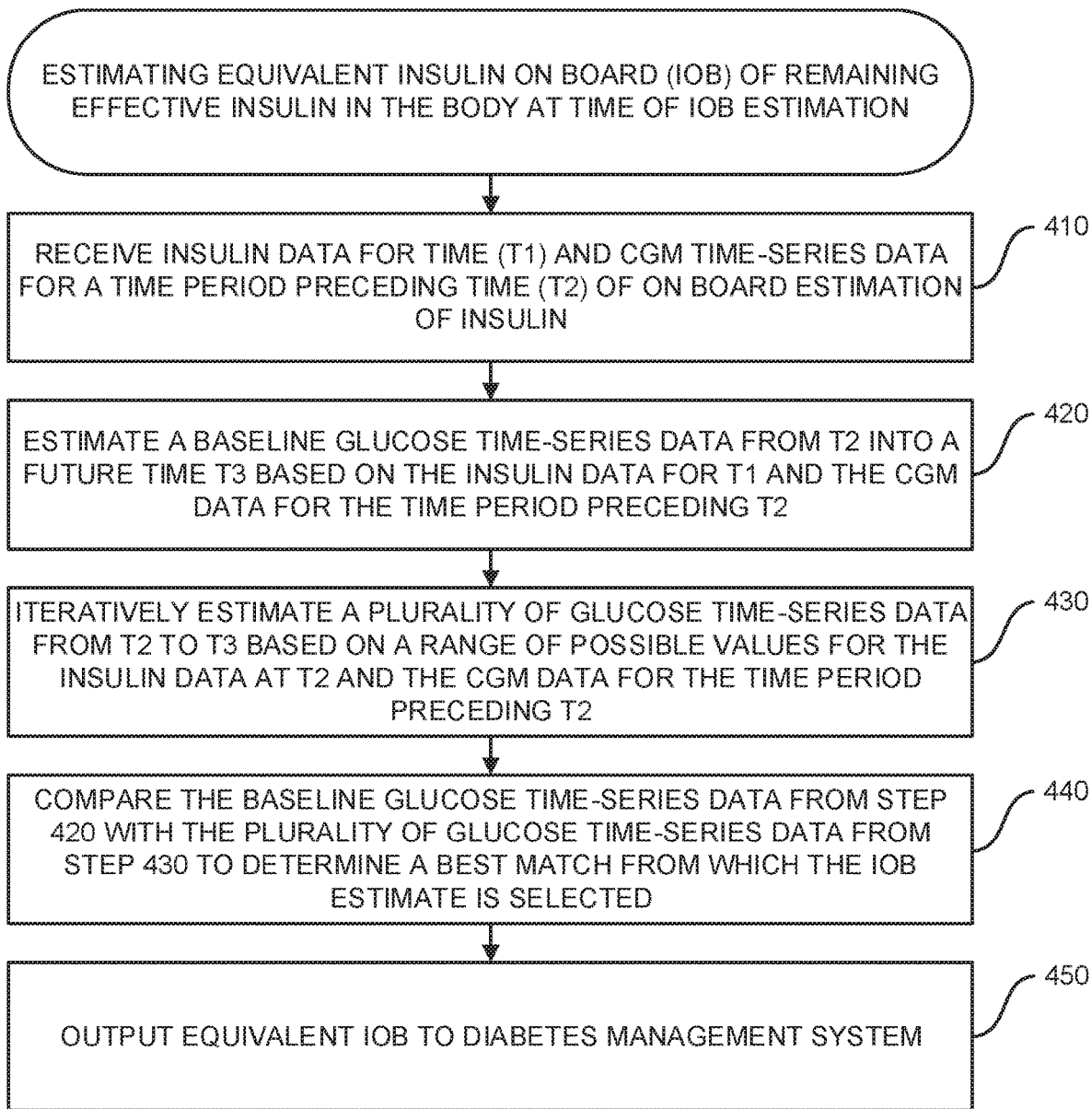
FIG. 4 is a flow diagram for a method for estimating equivalent insulin on board (JOB) of remaining effective insulin in the body at time of IOB estimation.

FIG. 4 is a flow diagram for a method 400 for estimating equivalent insulin on board (JOB) of remaining effective insulin in the body at time of IOB estimation (e.g., time T2).

At 410, insulin data is received for time T1 and CGM time-series data for a time period preceding time T2 of on board estimation of insulin. In some implementations, insulin data can be collected by a connected device, such as an insulin-pump or a connected insulin pen. Alternatively, insulin doses may be self-reported by the subject, e.g., logged using a phone application.

This operation relies on the ability to know accurate insulin dose information (or use estimated insulin dose information) and predict the future from CGM. Insulin dosing information may be reported or may be estimated especially if previous insulin dosing information is uncertain or unreliable.

IOB generally considers past insulin data as known and reliable. However, this may not always be the case, e.g., in patients that treat their diabetes with multiple daily injections (MDI). In the same way that equivalent COB can work without carbohydrates data, equivalent IOB can work without insulin data, e.g., with estimated insulin delivery. To the extent that an application relies on estimated insulin delivery, it becomes useful to carefully consider the time horizon for BG prediction.

At 420, similar to IOB at 120, a baseline glucose time-series data is estimated from time T2 into a future time T3 based on the insulin data for time T1 and the CGM data for the time period preceding time T2.

In some implementations, the predicted BG over a prediction horizon is computed as a function of CGM up to time T2, insulin up to time T2, and/or carbohydrates (if any) up to time T2.

In one exemplary approach, the estimator 330 explicitly estimates the subject's metabolic state at time T2 (using the same data), and then runs prediction based on that estimated state. In this example, prediction may be based on a model of the subject's state estimate (e.g., insulin-carb-glucose dynamics), which may or may not be specific to the subject (e.g., could be population-based or individualized).

Other exemplary models include subcutaneous oral glucose minimal model (SOGMM) of Hughes et al. or the "meal model" of Dalla Man et al., all of which are incorporated herein by reference in their entireties.

The duration of a prediction horizon is defined by a time T3, which is farther in the future than the end time of the residual effect of past insulin actions using CGM data, known or estimated insulin data (including the bolus at time T1), and optionally carbohydrates data.

Over a given prediction horizon, the prediction provides the subject's future BG from the current state estimate, fully accounting for the effect of known or estimated past insulin delivery.

There are many known methods for predicting glucose from time-series data. Predicting future glucose time-series may be based on the initial state informed by received/estimated carb/insulin values. Others are possible, such as physical activity data from an activity tracker.

At 430, similar to IOB at 130, a plurality of glucose time-series data is iteratively estimated from time T2 to time T3 based on a range of possible values for the insulin data at time T2 and the CGM data for the time period preceding time T2.

In some embodiments, iterative estimation includes predicting glucose time-data from time T2 to time T3 similar to 420, but instead: (1) ignoring the effect of known or estimated past insulin delivery (including the insulin dose at time(s) T1.0, T1.1, . . . ); and (2) inserting one or more from a set of candidate equivalent doses of insulin at time T2, and by comparing the additional future glucose time-series data set(s) with the first glucose time-series data set to identify a best match, thereby determining an equivalent IOB value at time T2 used to generate the best, thereby allowing for contextualizing the equivalent IOB estimate using the CGM time-series data during the time period of insulin action by iterating glucose time-series predictions based on CGM time-series data (during the time period of insulin action), ignoring past insulin up to time T2 and with candidate "equivalent" doses at time T2 (from about zero to about the actual bolus amount), looking for a best match to the baseline prediction. The best equivalent dose is the equivalent IOB estimate.

The effect of processing without or proceeding without (i.e., ignoring) past known or estimated insulin delivery (e.g., to make predictions without using data or information pertaining to past pharmacons, such as previous insulin injections for example) can be achieved in different ways. In general, predicted BG is computed as a function of CGM up to time T2, insulin up to time T2 (times T1.0, T1.1, . . . ), and carbohydrates (if any) up to time T2. Predictions that ignore the effect of known or estimated past insulin delivery would use this mapping but with the known or estimated past insulin set to zero. Thus, past pharmacon delivery information is attenuated (i.e., the amounts of past pharmacon(s) delivered are attenuated), held back or otherwise withheld from the prediction method or model. For example, in a state-space method of predicting future blood glucose, the process can be reduced to (1) identifying the states of the model that account for past insulin delivery (insulin in transit from the site of injection/infusion to the site or sites of action), (2) setting the value of these states to zero, and (3) deriving the prediction from the modified estimate of the subject's metabolic state at time T2.

At 440, the baseline glucose time-series data from step 420 is compared with the plurality of glucose time-series from step 430 to determine a best match from which the IOB estimate is selected. Any known comparison technique may be used.

In an implementation, prediction of future glucose time services can be repeated based on a range of possible insulin delivery values (e.g., equivalent IOB values) in place of the estimated insulin values of previous step. The glucose time-series prediction based on the initial insulin state values is compared with each of the glucose time-series predictions based on the range of possible insulin (bolus) amounts from the previous step, and the best match therebetween is identified. Depending on the implementation, this may be a comparison of a specific value at a specific time in the future or a comparison of a time-series using a function approach.

The resulting equivalent IOB assessment is a function of both recent insulin delivery and recent CGM, and adapts itself to the effect of recently delivered insulin that may have been absorbed by the subject faster or slower than what would be predicted by an open-loop nominal "action curve".

In other words, the technique calculates equivalent amount of IOB that matches the individualized prediction.

This method of calculation dynamically adapts to transient effects on IOB (e.g., sickness, cycles, stress, etc.) due to current CGM (prediction) as the comparison upon which the IOB is determined. This method also accommodates deviations in pharmacokinetic/pharmacodynamic (PK/PD) effect of insulin and carbohydrates around the subject's nominal action/absorption curves.

The best match between the baseline prediction and a prediction that ignores past insulin (up to time T2) with a candidate equivalent dose at time T2 is based on a distance metric (fit quality, optimization criterion) that compares the baseline predicted BG trajectory to the candidate equivalent predicted trajectory. The distance metric can be computed in many ways, including (1) computing the magnitude of the difference in predicted values at time T3, and (2) computing a weighted sum of square differences between time T2 and time T3, for example.

Alternatively, the time-series can be compared using "p"-norms: e.g., p=1 (weighted sum of absolute differences between time T2 and time T3), p=infinity (weighted max error between time T2 and time T3). Other measures of similarity between traces can be applied, such as Fourier series coefficients, auto-regressive properties of the series, dynamic time-warping, and edit distance, for example. It may also include other forms of categorization including clustering analysis, i.e., two time-series have a good match if they belong to the same cluster.

The process of identifying the best match can be iterative in a serial implementation of the method or done in parallel for computational speed.

In an implementation, the discrete insulin bolus is computed that would have to be taken right now to create a match between (1) full state predicted BG and (2) predicted BG from the state estimate with insulin in transit zeroed-out. This "matching" bolus is equivalent IOB.

At 450, the equivalent IOB is outputted to a diabetes management system. The insulin value used in the best match scenario glucose time-series prediction is outputted.

Figure 5:
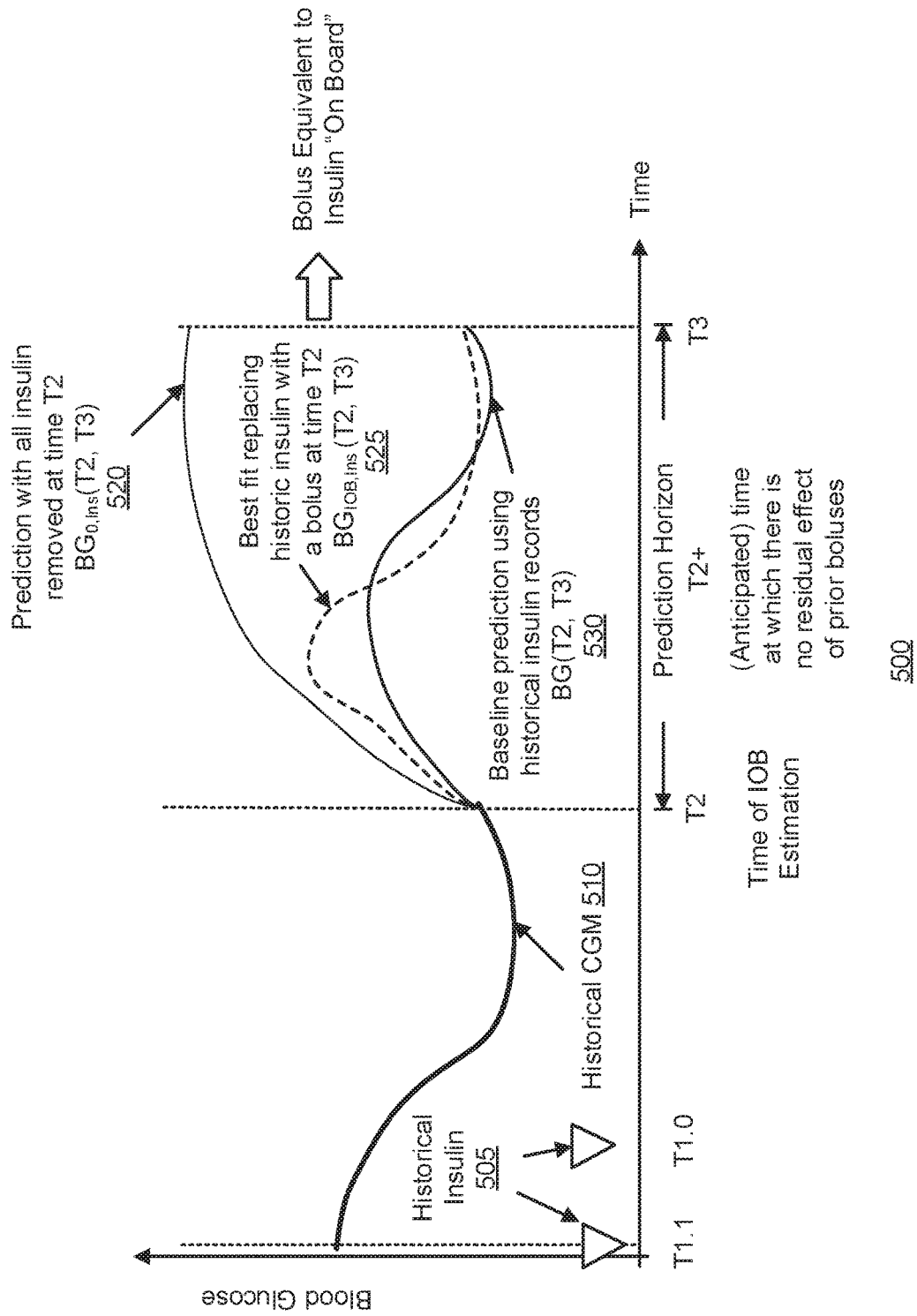
FIG. 5 represents how the XOB calculation is adapted to the problem of estimating IOB.

With respect to bolus equivalent IOB, FIG. 5 represents how the XOB calculation is adapted to the problem of estimating IOB. The historical CGM line 510 and the baseline prediction line 530 are similar to the lines 210 and 230 of FIG. 2, respectively, and their descriptions are omitted for brevity.

Times T1.1 and T1.0 represent the times of the last insulin injections/infusions (the historical insulin represented by the triangles 505) that are still in effect at the time IOB is requested (time T2).

For IOB estimation, the prediction horizon is some time beyond the anticipated time at which there is no residual effect of past insulin injections/infusions (time T2+). This can be predetermined based on a conservative estimate of insulin action across the population or any other method of determining insulin action for a patient.

The line 520 corresponds to a prediction where all remaining historically injected/infused insulin action/amounts have been removed. This explains the apparent rise in glucose concentration.

The dashed line 525 corresponds to the best match to the baseline prediction (line 530) obtained by replacing all remaining historically injected/infused insulin (represented by the triangles 505) with a bolus at time T2. The bolus producing this best match is the IOB estimate.

Note that initially the IOB estimate differs greatly from the baseline prediction. This is due to the specifics of the method. At time T2, historical doses injected at times T1.0, T1.1 are removed and replaced with a new dose of IOB administered at time T2. Because the new dose needs some time to be absorbed and have any glucose-regulating effect, glucose will appear to rise faster than the baseline estimation, where insulin is already partially absorbed and active.

Figure 6A:
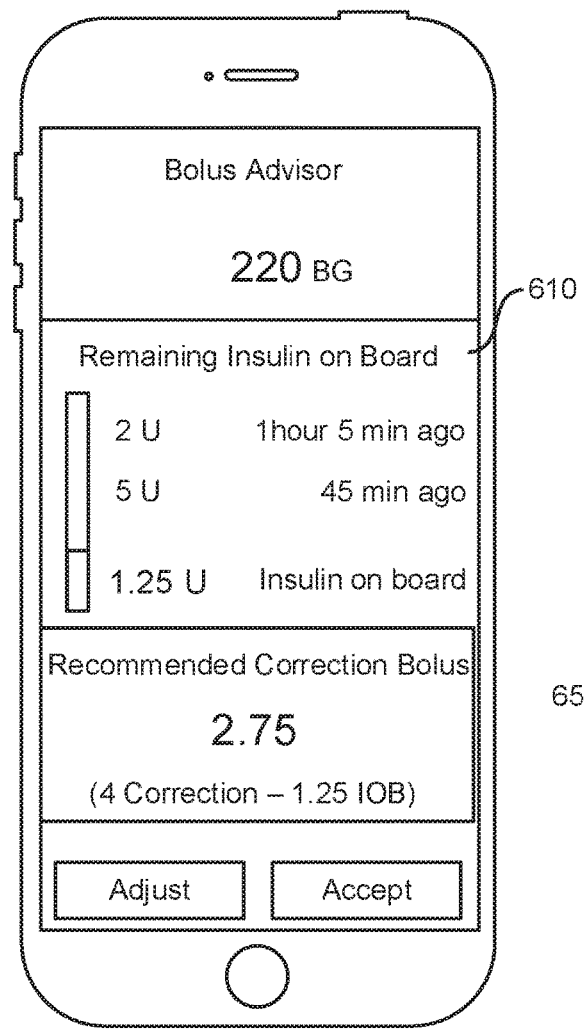
FIG. 6A describes a possible mechanism to display IOB for a continuous glucose monitoring (CGM) system and/or pen user requesting advice on a correction bolus.

FIG. 6A describes a possible mechanism to display IOB on a mobile computing device 600 for a CGM/pen user requesting advice on a correction bolus. The display 610 can display the history of boluses as well as the remaining IOB.

Figure 6B:
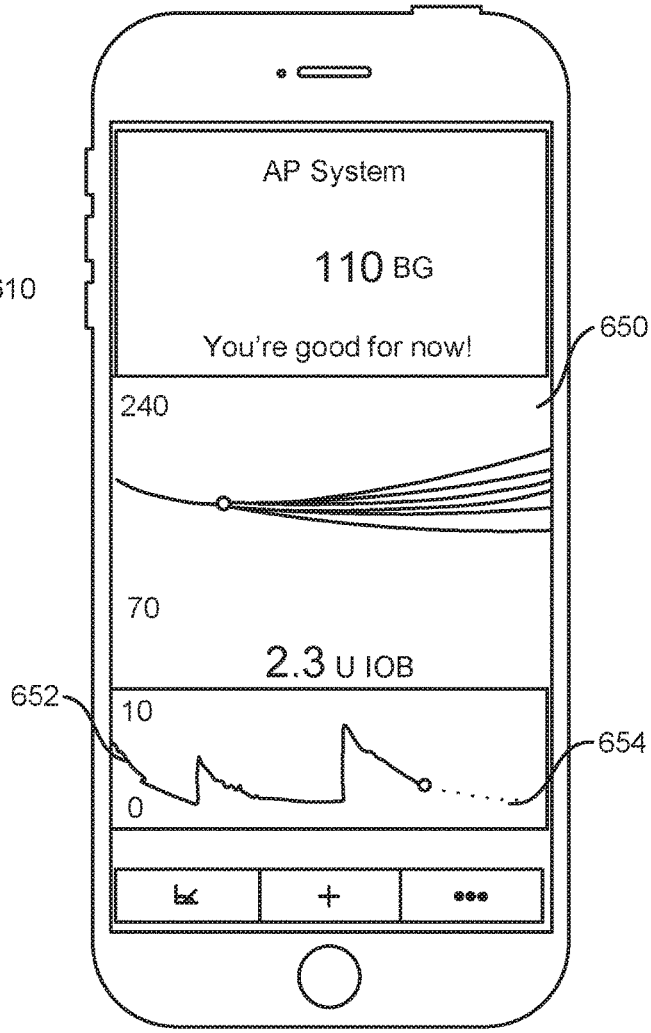
FIG. 6B shows how an artificial pancreas (AP) will update its estimate of IOB every time insulin delivery is computed.

FIG. 6B describes an IOB display 650 on a mobile computing device 640 as it could be presented in an AP system. In this case, IOB can be continuously updated and displayed as a time-series (line 652). Potentially, a prediction of future IOB values could be displayed (dotted line 654). The current value of IOB (in this case 2.3 U) is displayed. As illustrated in FIG. 6B, an AP will update its estimate of IOB every time insulin delivery is computed. In this embodiment, IOB can be presented as a time-series.

The IOB informs the bolus calculator by adapting the assessment to a baseline recommendation, or a bolus recommendation without a known or reliable estimate of IOB) to ensure optimality of the final result. For example, if a particular meal requires a 4 unit bolus (i.e., the baseline recommendation), and 1 unit IOB is estimated (using the systems and methods described herein), then the final bolus should be 3 units, wherein a correction of the baseline recommendation is made by subtracting the IOB estimate from the baseline insulin recommendation. This can be done automatically as an input (subtraction from final) in any standard bolus calculator without an IOB subtraction already.

Figure 6C:
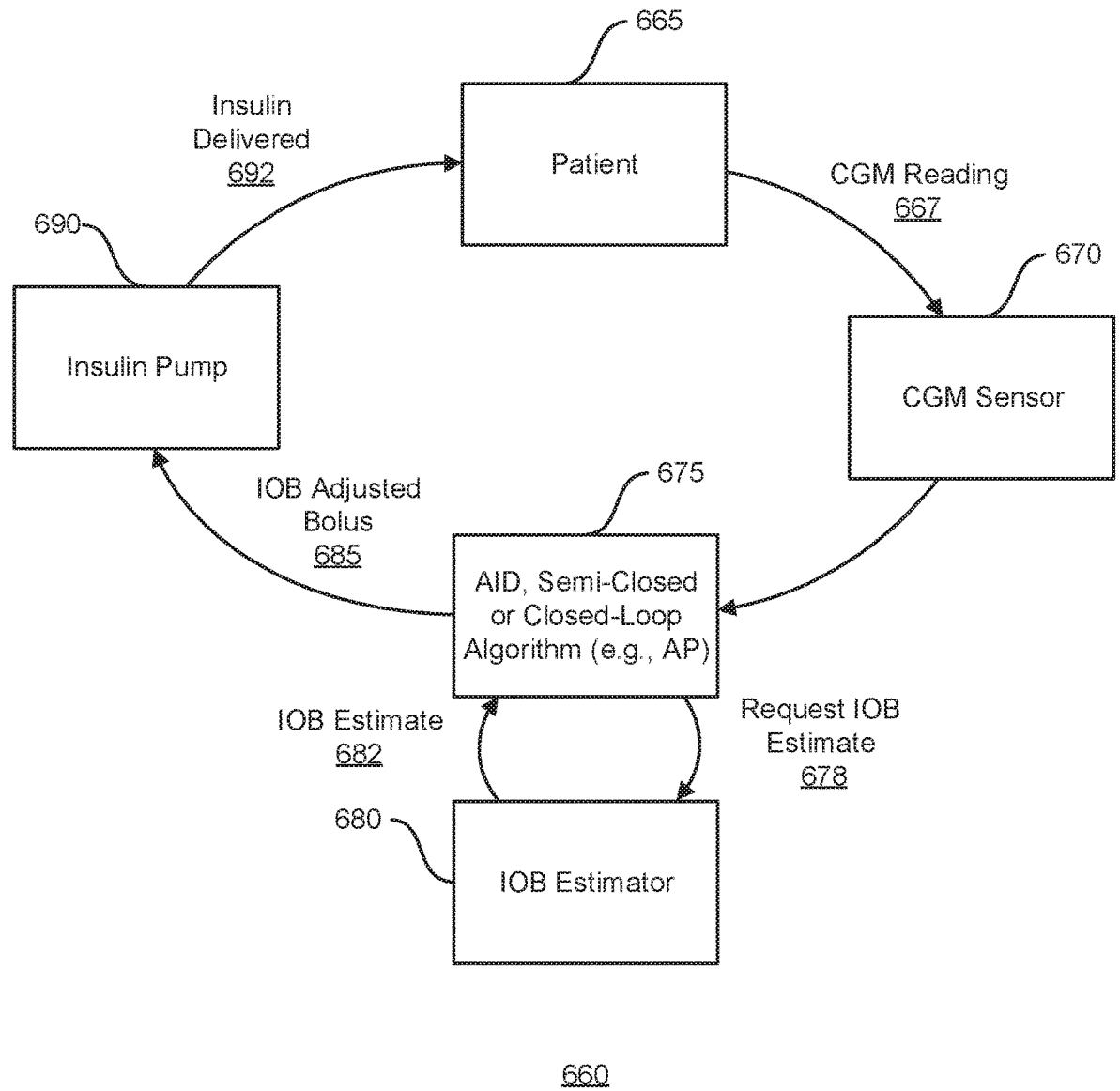
FIG. 6C is a diagram that describes the use of an insulin on board estimator in conjunction with an automated insulin delivery (AID) algorithm.

FIG. 6C is a diagram 660 that describes the use of the insulin on board estimator in conjunction with an automated insulin delivery (AID) algorithm, i.e., a semi closed-loop or closed-loop algorithm, or any algorithmic recommendation system. In some implementations, the AID, semi-closed loop, or closed loop algorithm 675 is comprised within a computing device. Every interval of time (e.g., every 1 minute, every 2 minutes, every 5 minutes, every 10 minutes, etc.), a CGM sensor obtains an updated estimate of the glucose concentration of the patient 665 as a CGM reading 667. In one example, CGM sensor information is provided to the AID, semi-closed loop, or closed loop algorithm 675, such as an AP algorithm, which computes a desired insulin dose. The algorithm 675 calls the IOB estimator 680 with a request for an IOB estimate 678 to produce an IOB estimate 682. The IOB estimate is subtracted from the desired insulin dose to compute the final bolus recommendation (i.e., an IOB adjusted bolus 685). This estimate is provided to an insulin pump 692, which then delivers insulin 692 to the patient 665. This completes the AID cycle, which is repeated periodically (e.g., in the next 1 minute, in the next 2 minutes, in the next 5 minutes, in the next 10 minutes, etc.).

Figure 7:
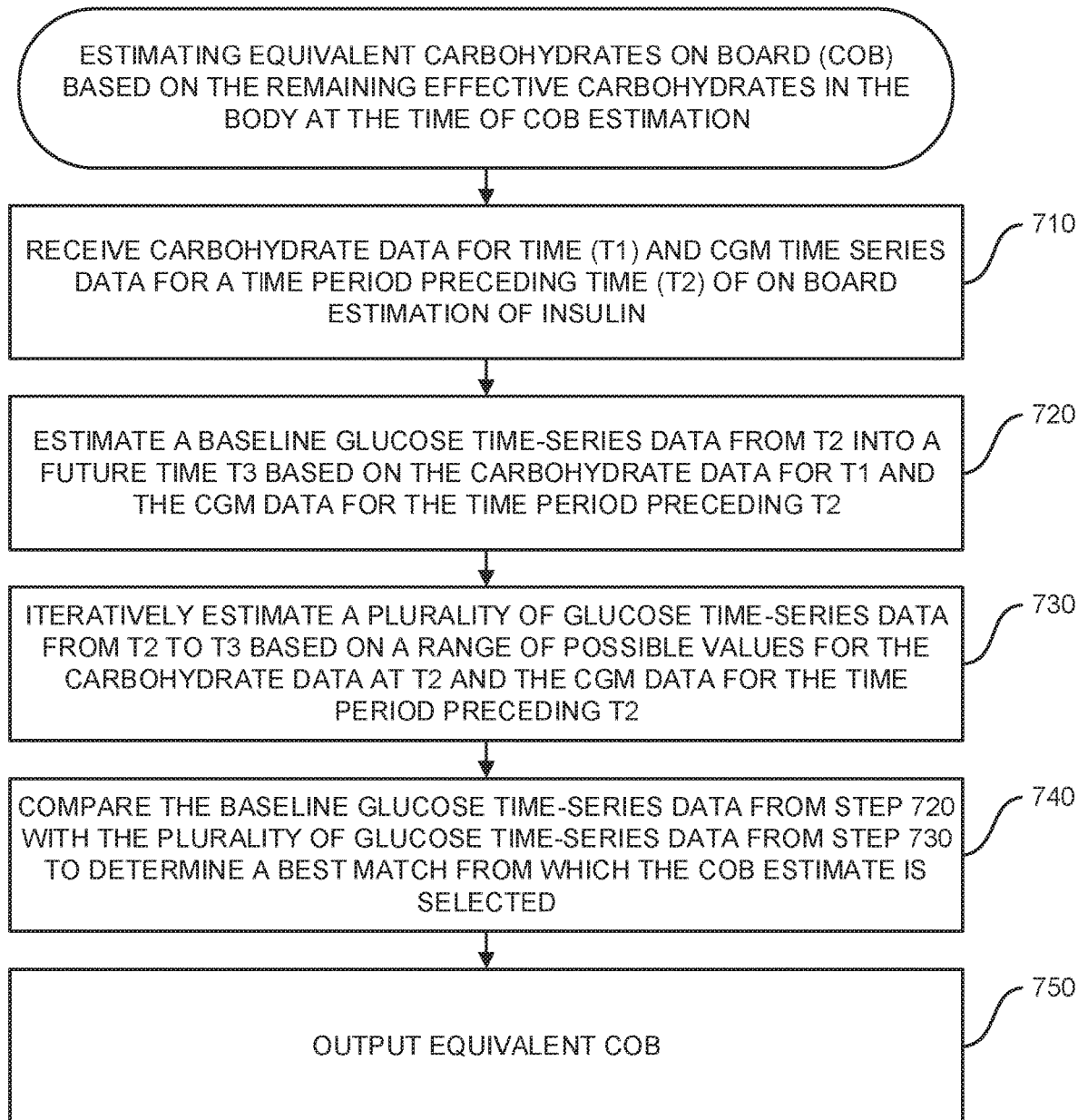
FIG. 7 is a flow diagram that illustrates a method wherein the pharmacon is carbohydrates, whereby carbohydrates on board (COB) has been requested.

FIG. 7 is a flow diagram that illustrates a method 700 wherein the pharmacon is carbohydrates, whereby COB has been requested (e.g., by a subject, by a software application, etc.). A COB calculation is often difficult to estimate as subjects often eat different meal types, sizes, and frequencies. For a person with diabetes to make regular daily determinations of an amount of insulin to bolus for a given meal, they generally use a bolus calculator. Bolus calculators currently use a complex set of settings (including insulin type/active insulin duration, carb-to-insulin ratio, and insulin correction factor) that a user must determine (or accept generic non-personalized defaults) that are used, together with real-time inputs, including current blood glucose value and carb estimates, which are input into a formula, from which an insulin bolus recommendation can be calculated. Alternatively, some patients may mentally estimate a number of units of insulin for a given meal (e.g., "that's a 5 unit bowl of soup" or "that's a 10 unit meal"). In either case, any "leftover carbohydrates," i.e., previously eaten meal without insulin to sufficiently cover are not necessarily considered, except for what may be assumed from the blood sugar level (e.g., a high blood sugar suggests remaining carbohydrates on board).

Accordingly, the systems and methods described herein dynamically estimate equivalent COB based on the remaining effective carbohydrates in the body. Equivalent COB may be dynamically estimated on demand from known or reported ingestion of carbohydrates and glucose time-series data associated therewith. This provides a better assessment of COB informed by previous carbohydrates (and optionally insulin doses) and glucose time-series data.

The method 700 adapts to other effects on COB (i.e., differences in absorption of carbohydrates due to time of day, composition of meal (fat/protein), etc.) due to current CGM (prediction) as the comparison upon which the COB is determined.

At 710, carbohydrate data is received for time T1 and CGM time-series data is received for a time period preceding time T2 of on board estimation of insulin. The time scale issue is important for carbohydrates because estimation of meal timing may not be accurately known. The carbohydrate data may be received from user input or may be estimated by a computing device depending on the implementation. The CGM time-series data provides a real-time prediction of future glucose over a period of carbohydrate absorption. In some implementations, an individualized model of the subject or a predictor based on a population-based model may also be used, depending on the implementation.

At 720, baseline glucose time-series data is estimated from time T2 into a future time T3 based on the carbohydrate data for time T1 and the CGM data for the time period preceding time T2. The current CGM time-series is used to predict the future. In some implementations, an individualized model or a population-based model may be used.

At 730, a plurality of glucose time-series data is iteratively estimated from time T2 to time T3 based on a range of possible values for the carbohydrate data at time T2 and the CGM data for the time period preceding time T2. Current CGM time-series is used to predict the future. In some implementations, an individualized model may be used.

At 740, the baseline glucose time-series data from 720 is compared with the plurality of glucose time-series from 730 to determine a best match from which the COB estimate is selected. In this manner, a net equivalent amount of carbohydrates at time t=0 that best matches the individualized prediction is determined. The equivalent amount of COB that matches the individualized prediction is calculated.

At 750, the equivalent COB is outputted, e.g., onto a display, into a bolus calculator, into an artificial pancreas system, for use in behavioral modeling, for use in behavioral learning and assessment, etc.

Figure 8:
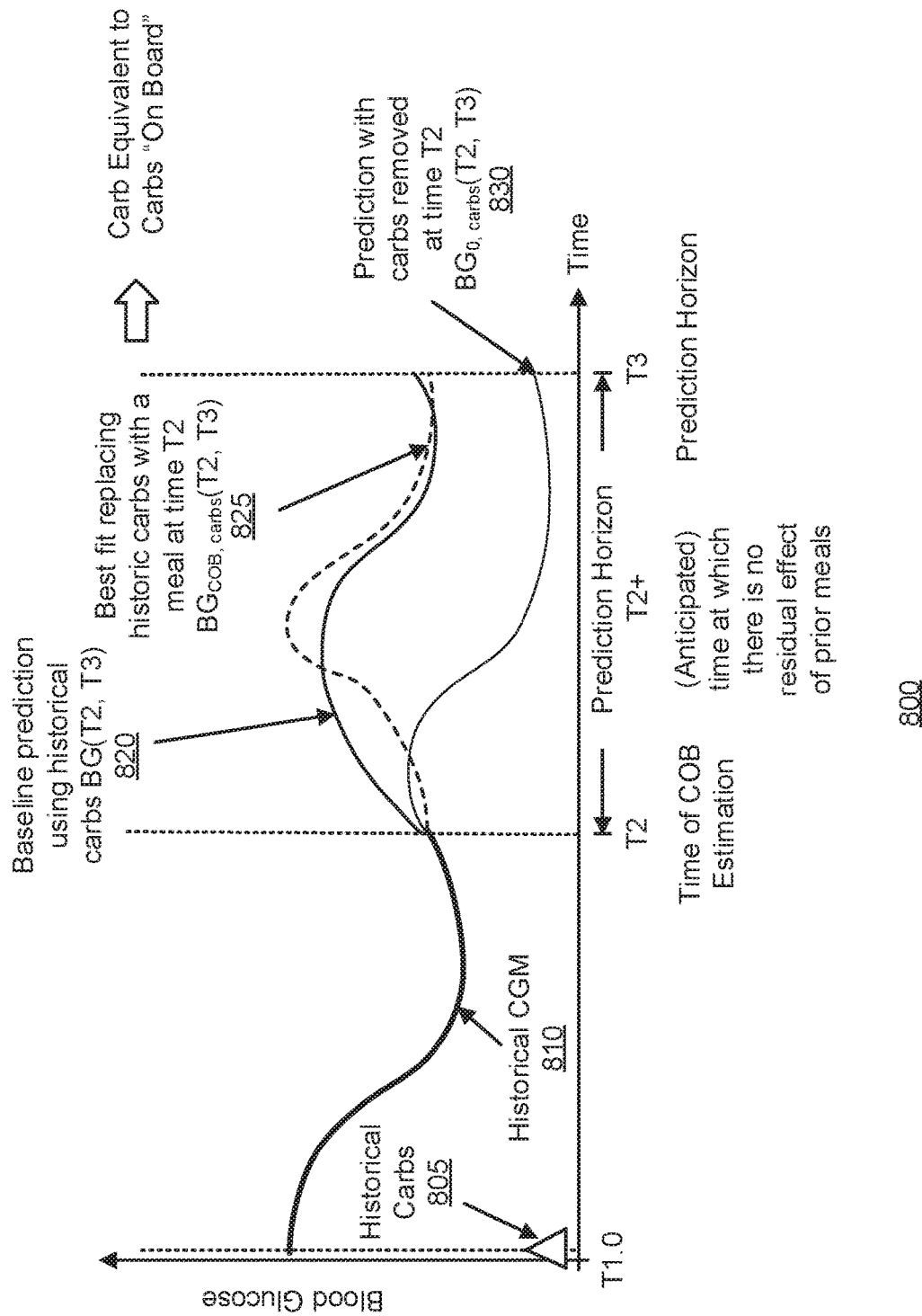
FIG. 8 is a graph that represents an adaptation of FIG. 2 to the problem of estimating COB.

FIG. 8 is a graph 800 that represents an adaptation of FIG. 2 to the problem of estimating COB. The lines 810 and 820 are similar to the lines 210 and 230, respectively, and their descriptions are omitted for brevity. The line 830 represents the predicted glucose effect of removing all carbohydrates on board at the time the estimate is requested (i.e., time T2). The line 825 represents the best match prediction produced by replacing all carbohydrates on board with a meal at time T2. The amount of carbohydrates resulting in this best matching curve are the equivalent COB. The assumption is that at time T1 a meal was ingested which has not been fully metabolized at time T2, but will be fully absorbed by some time T2+ prior to the prediction horizon ends (e.g., time T3).

Figure 9:
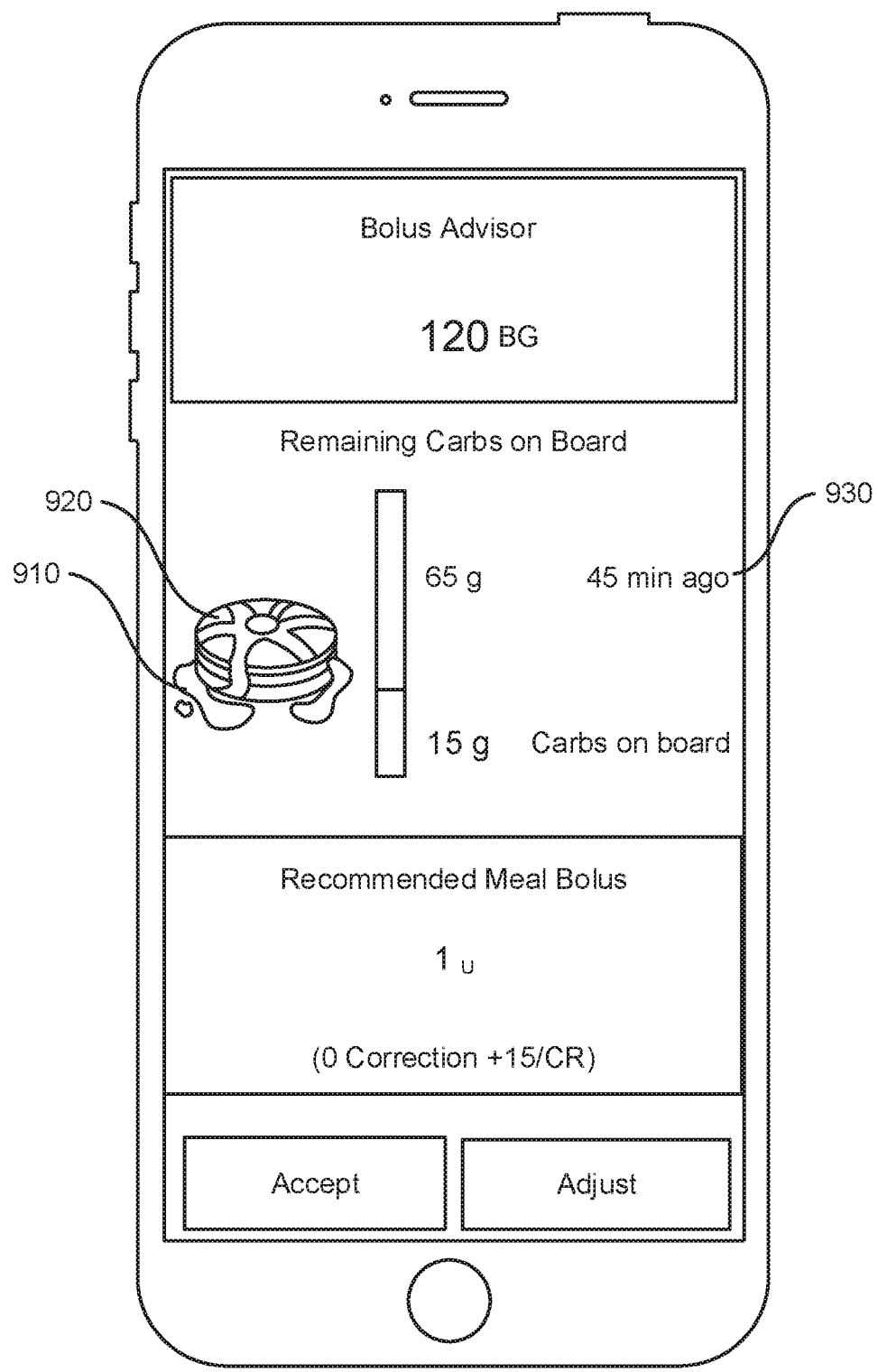
FIG. 9 is an example display of COB information to a user.

FIG. 9 is an example display 900 of COB information to the user. If the user enters information pertaining to a meal, such as a picture or other representation (e.g., textual, visual, graphical, etc.), the fraction of the meal remaining is displayed in solid 910, while the parts estimated to be already metabolized are translucent 920. In addition, data 930, such as the amount and times of recent meals (e.g., acknowledged by the user, estimated by the subject, etc.) is presented to the user. Other methods of displaying COB may be appreciated by one skilled in the art.

Figure 10A:
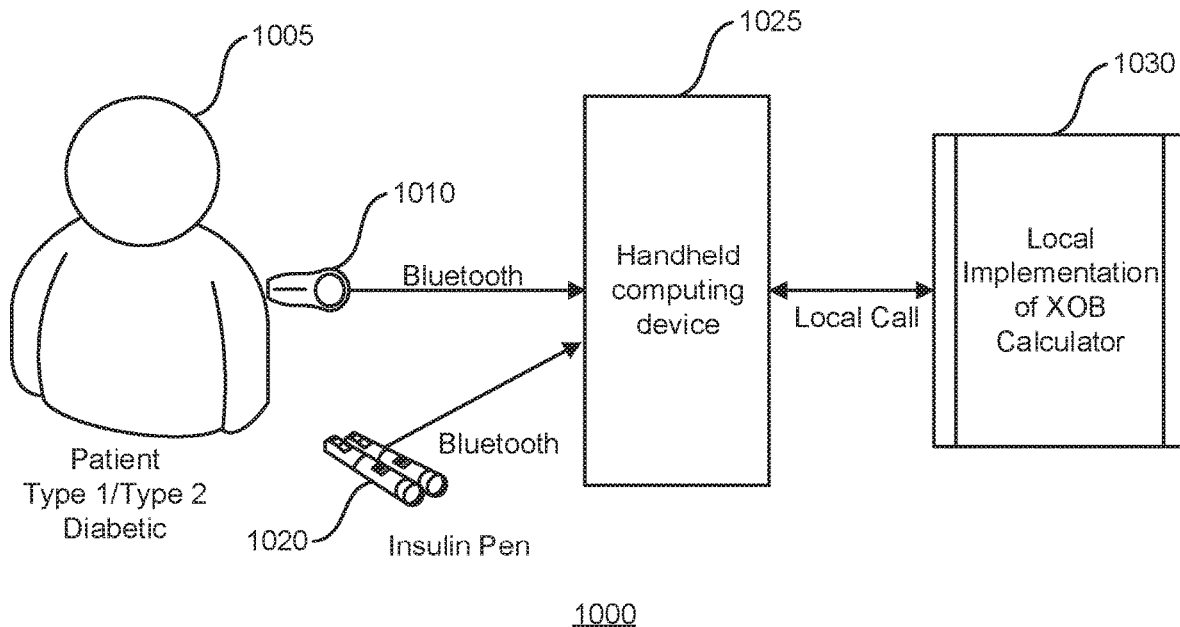
FIGS. 10A and 10B show an example of a CGM system/pen combination system with a local implementation, and with a cloud implementation, respectively.
Figure 10B:
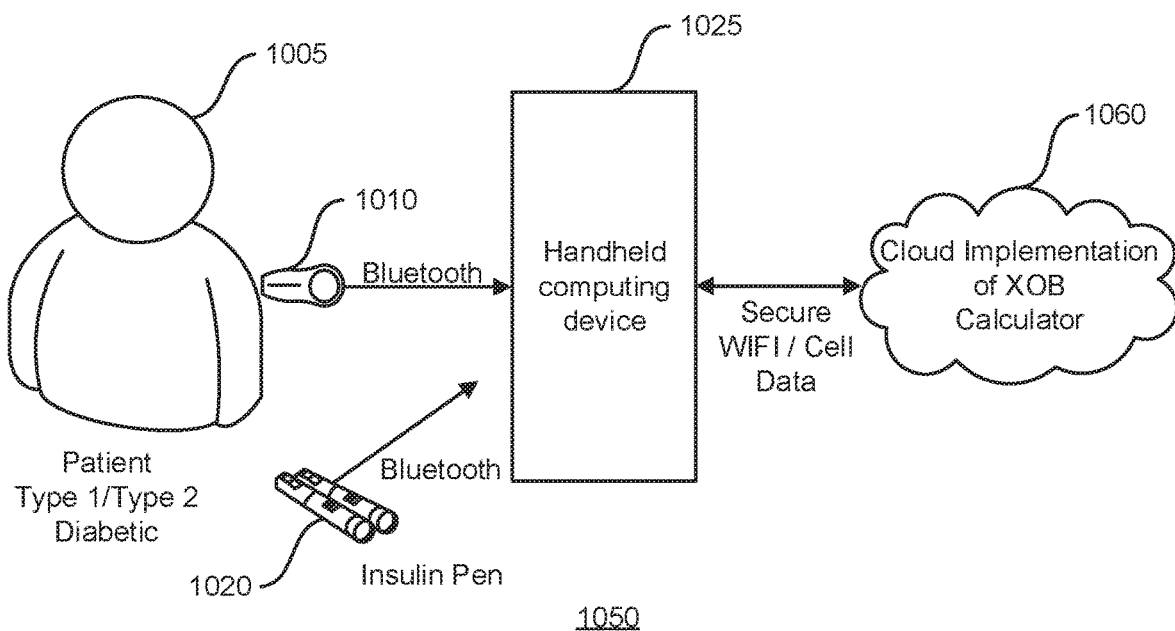

FIGS. 10A and 10B show an example of a CGM/pen combination system with a local implementation 1000 of the methods and systems described herein, and a cloud implementation 1050, respectively.

Figure 13:
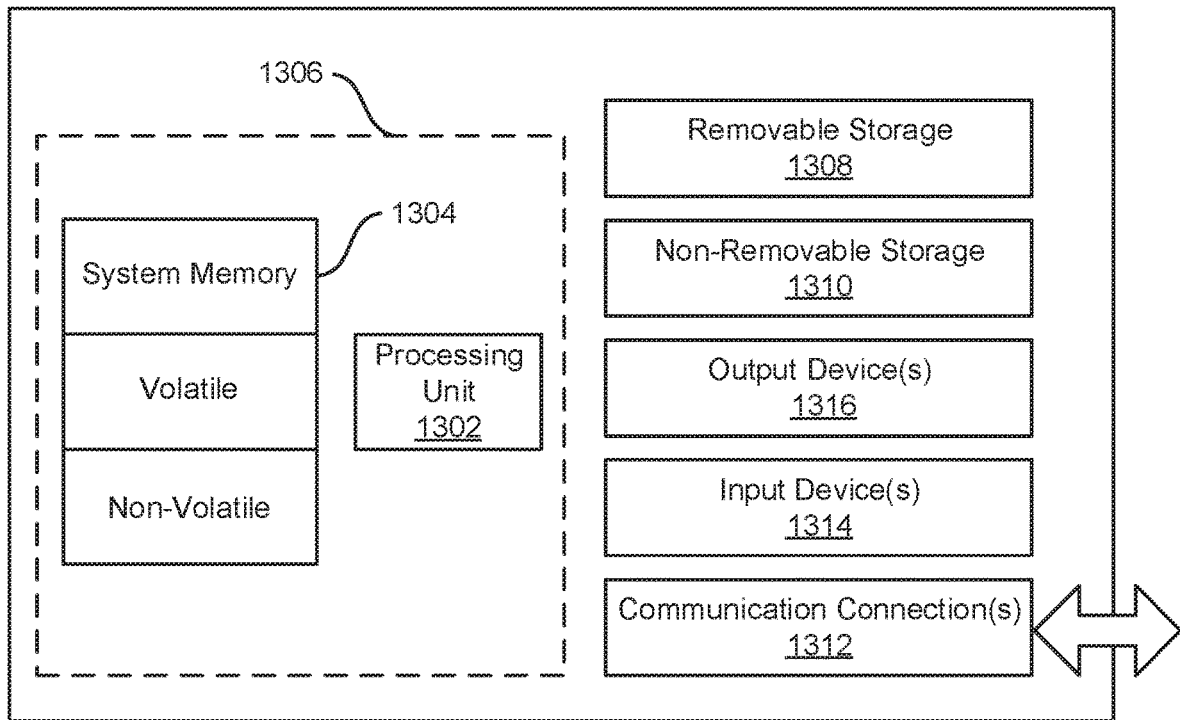
FIG. 13 shows an exemplary computing environment in which example embodiments and aspects may be implemented.

In FIG. 10A, a subject 1005 (also referred to as a patient) uses a monitoring device 1010 which provides the appropriate data to a handheld computing device 1025 (via Bluetooth for example). In some implementations, alternatively or additionally, an insulin pen 1020 may provide data to the handheld computing device 1025 (via Bluetooth for example). The handheld computing device 1025 receives the data, and in conjunction with a local implementation of an XOB calculator 1030 such as the XOB estimator 330 described herein, performs the calculations, determinations, and estimations described herein and provides the appropriate output, e.g., via a display of the handheld computing device 1025. The local implementation of an XOB calculator 1030 may be comprised within the handheld computing device 1025 and/or accessible via a local call. The handheld computing device 1025 may be implemented using a variety of computing devices such as smartphones and tablets. Other types of computing devices may be supported. A suitable computing device is illustrated in FIG. 13 as the computing device 1300.

FIG. 10B is similar to FIG. 10A. However, instead of the handheld computing device 1025 making a local call to the XOB calculator 1030 to perform the calculations, determinations, and estimations described herein, the XOB calculator 1060 is implemented in the cloud. Accordingly, the handheld computing device 1025 communicates with the cloud implementation of the XOB calculator 1060 via a network connection, such as a secure Wi-Fi or cellular network.

Figure 11:
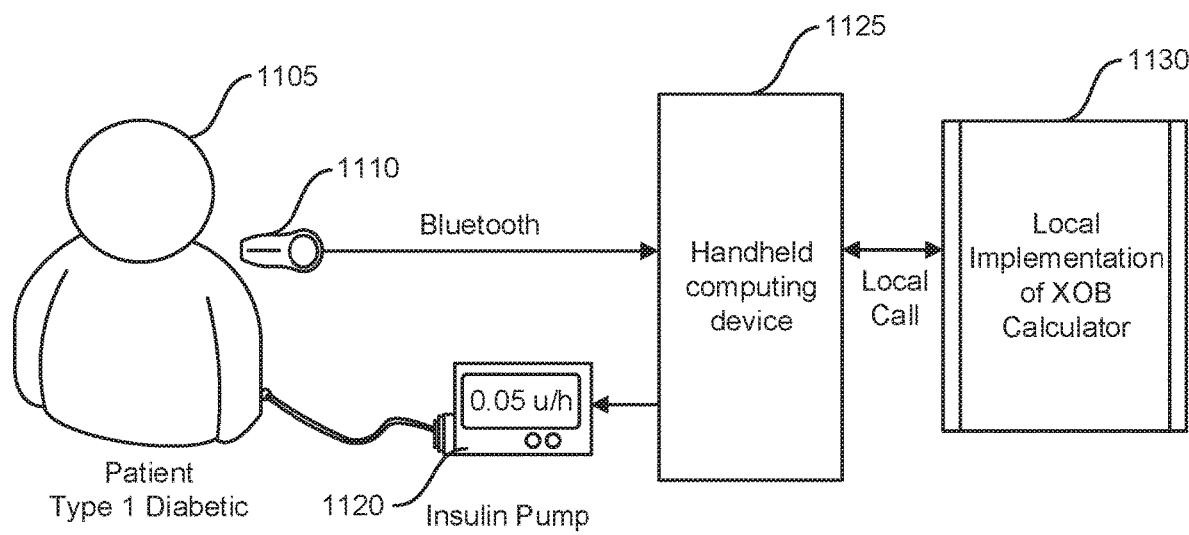
FIG. 11 is an example of an AP implementation.

FIG. 11 is an example of an AP implementation 1100 of the methods and systems described herein. The method is implemented as a local library called by the AP algorithm to estimate IOB when meals are announced by the user, a meal is automatically detected, or a correction bolus is deemed necessary.

In FIG. 11, a subject 1105 (also referred to as a patient) uses a monitoring device 1110 which provides the appropriate data to a handheld computing device 1125 (via Bluetooth for example). Similar to FIG. 10A, the handheld computing device 1125 receives the data, and in conjunction with a local implementation of an XOB calculator 1130 such as the XOB estimator 330 described herein, performs the calculations, determinations, and estimations described herein and provides the appropriate output, e.g., via a display of the handheld computing device 1125. The local implementation of an XOB calculator 1130 may be comprised within the handheld computing device 1125 and/or accessible via a local call.

Moreover, the handheld computing device 1125 provides data to an insulin pump 1120, which may then adjust and/or provide an appropriate insulin amount to the subject 1105 based on the determinations made by the handheld computing device 1125 in conjunction with the XOB calculator 1130.

The handheld computing device 1125 may be implemented using a variety of computing devices such as smartphones and tablets. Other types of computing devices may be supported. A suitable computing device is illustrated in FIG. 13 as the computing device 1300.

Figure 12:
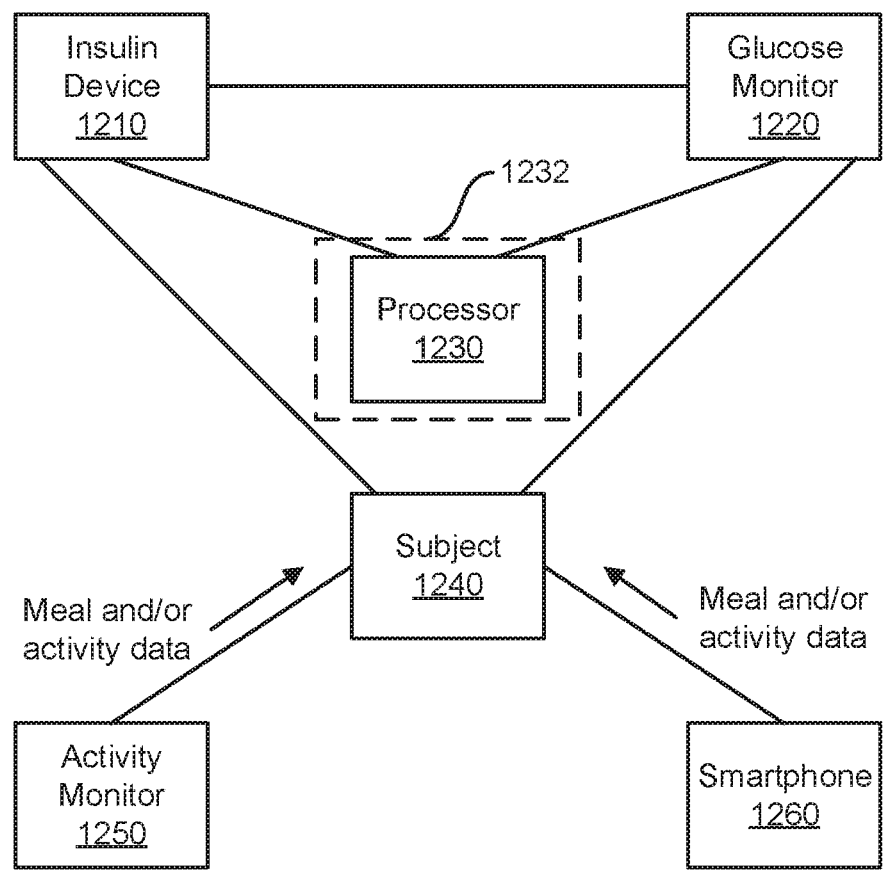
FIG. 12 is a high level functional block diagram of an embodiment of the invention.

FIG. 12 is a high level functional block diagram 1200 of an embodiment of the invention. A processor 1230 communicates with an insulin device 1210 and a glucose monitor 1220. The insulin device 1210 and the glucose monitor 1220 communicate with a subject 140 to deliver insulin to the subject 1240 and monitor glucose levels of the subject 1240, respectively. The processor 1230 is configured to perform the calculations described further herein. The insulin device 1210 and the glucose monitor 1220 may be implemented as separate devices or as a single device, within a single device, or across multiple devices. The processor 1230 can be implemented locally in the insulin device 1210, the glucose monitor 1220, the activity monitor 1250, the smartphone 1260 or as standalone device shown with dashed lines as standalone device 1232 (or in any combination of two or more of the devices). The processor 1230 or a portion of the system can be located remotely such as within a server or a cloud-based system.

Examples of insulin devices, such as the insulin device 1210, include insulin syringes, external pumps, and patch pumps that deliver insulin to a subject, typically into the subcutaneous tissue. Insulin devices 1210 also includes devices that deliver insulin by different means, such as insulin inhalers, insulin jet injectors, intravenous infusion pumps, and implantable insulin pumps. In some embodiments, a subject will use two or more insulin delivery devices in combination, for example injecting long-acting insulin with a syringe and using inhaled insulin before meals. In other embodiments, these devices can deliver other drugs that help control glucose levels such as glucagon, pramlintide, or glucagon-like peptide-1 (GLP-1).

Examples of a glucose monitor, such as the glucose monitor 1220, include continuous glucose monitors that record glucose values at regular intervals, e.g., 1, 5, or 10 minutes, etc. These continuous glucose monitors can use, for example, electrochemical or optical sensors that are inserted transcutaneously, wholly implanted, or measure tissue non-invasively. Examples of a glucose monitor, such as the glucose monitor 1220, also include devices that draw blood or other fluids periodically to measure glucose, such as intravenous blood glucose monitors, microperfusion sampling, or periodic finger sticks. In some embodiments, the glucose readings are provided in near real-time. In other embodiments, the glucose reading determined by the glucose monitor can be stored on the glucose monitor itself for subsequent retrieval.

The insulin device 1210, the glucose monitor 1220, and the standalone device 1232 may be implemented using a variety of computing devices such as smartphones, desktop computers, laptop computers, and tablets. Other types of computing devices may be supported. A suitable computing device is illustrated in FIG. 13 as the computing device 1300 and cloud-based applications.

The insulin device 1210, the glucose monitor 1220, and the standalone device 1232 may be in communication through a network. The network may be a variety of network types including the public switched telephone network (PSTN), a cellular telephone network, and a packet switched network (e.g., the Internet). Although only one insulin device 1210, one glucose monitor 1220, and one processor 1230 (within one standalone device 1232) are shown in FIG. 12, any number of insulin devices, glucose monitors, processors, and standalone devices may be supported, nor how the disparately shown devices may be combined. An activity monitor 1250 and/or a smartphone 1260 may also be used to collect meal and/or activity data from or pertaining to the subject 1240, and provide the meal and/or activity data to the processor 1230.

The processor 1230 may execute an operating system and one or more applications. The operating system may control which applications are executed by the insulin device 1210, the glucose monitor 1220, and the standalone device 1232, as well as control how the applications interact with one or more sensors, services, or other resources of the insulin device 110, the glucose monitor 1220, and the standalone device 1232.

The processor 1230 receives data from the insulin device 1210 and the glucose monitor 1220, as well as from the subject 1240 in some implementations, and performs a replay analysis that evaluates the patient's current meal bolusing strategy and compares it to alternative bolusing times and insulin amounts.

FIG. 13 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 13, an exemplary system for implementing aspects described herein includes a computing device, such as computing device 1300. In its most basic configuration, computing device 1300 typically includes at least one processing unit 1302 and memory 1304. Depending on the exact configuration and type of computing device, memory 1304 may be volatile (such as random access memory (RAM)), non-volatile (such as read-only memory (ROM), flash memory, etc.), or some combination of the two. This most basic configuration is illustrated in FIG. 13 by dashed line 1306.

Computing device 1300 may have additional features/functionality. For example, computing device 1300 may include additional storage (removable and/or non-removable) including, but not limited to, magnetic or optical disks or tape. Such additional storage is illustrated in FIG. 13 by removable storage 1308 and non-removable storage 1310.

Computing device 1300 typically includes a variety of computer readable media. Computer readable media can be any available media that can be accessed by the device 2100 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 1304, removable storage 1308, and non-removable storage 1310 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1300. Any such computer storage media may be part of computing device 1300.

Computing device 1300 may contain communication connection(s) 1312 that allow the device to communicate with other devices. Computing device 1300 may also have input device(s) 1314 such as a keyboard, mouse, pen, voice input device, touch input device, etc. Output device(s) 1316 such as a display, speakers, printer, etc. may also be included. All these devices are well known in the art and need not be discussed at length here.

In an embodiment, a system comprises an input compiler configured to receive and process input data; an exogenous pharmacon on board (XOB) estimator; and an output compiler.

In some embodiments, the input data corresponds to glucose concentration readings provided by a continuous glucose monitoring (CGM) system, insulin injection/infusion data, data on ingested meals, glucagon or other pharmacon dose and/or injection data, exercise data, or stress data. Alternatively or additionally, the input data comprises data pertaining to insulin, and/or the input data comprises data pertaining to carbohydrates.

Some embodiments further comprise a continuous glucose monitoring (CGM) system in communication with the input compiler and configured to provide the input data to the input compiler. Alternatively or additionally, a closed-loop delivery system is provided in communication with the input compiler and configured to provide the input data to the input compiler. In some embodiments, the input data comprises a sequence of insulin dose recommendations or glucagon dose recommendations.

In some embodiments, the input compiler is configured to compile at least one of (1) data related to a pharmacon whose glucose-effect equivalent is being compiled or (2) data related to the relevant history of continuous glucose monitoring (CGM) system readings.

In some embodiments, the output compiler is an XOB output compiler configured to render an XOB estimation. The XOB estimation may comprise an insulin on board (JOB) estimation and/or a carbohydrates on board (COB) estimation.

In some embodiments, the XOB estimator is configured to estimate the glucose equivalent effect of the pharmacon at a predetermined time. Alternatively or additionally, the XOB estimator comprises a baseline time-series estimator, an iterative time-series comparator, and a time-series comparator. The baseline time-series estimator may be a stateless machine that receives historical XOB amounts and continuous glucose monitoring (CGM) system history and produces a time-series that approximates future values of glucose. The iterative time-series comparator is configured to combine a procedure that generates candidate XOB amounts with a modification of the time-series estimator in which historical XOB amounts are substituted with the XOB amount under consideration. The time-series comparator is configured to match a pair of time-series that can be any measure of distance or similarity between the series.

In an embodiment, a method comprises receiving exogenous pharmacon data for a time T1, and glucose time-series data for a time period preceding a time T2 of on board estimation of the pharmacon; estimating baseline glucose time-series data from the time T2 of XOB estimation into a time T3 based on the data for time T1 and continuous glucose monitoring (CGM) system data for the time period preceding T2; iteratively estimating a plurality of glucose time-series data from the time T2 to the time T3 based on a range of possible values for the data at the time T2 and the CGM data for the time period preceding T2; comparing the baseline glucose time-series data with the plurality of glucose time-series to determine a best match from which an exogenous pharmacon on board (XOB) estimate is selected; and outputting the XOB estimate.

In some embodiments, the exogenous pharmacon data is received from one of a subject or a connected device. Alternatively or additionally, the exogenous pharmacon data comprises insulin on board (JOB), and/or the connected device is an insulin pump. Alternatively or additionally, the exogenous pharmacon data comprises carbohydrates on board (COB).

In some embodiments, the method further comprises removing at least one of non-reliable data or spurious data from the exogenous pharmacon data and the glucose time-series data. At least one of the exogenous pharmacon data or the glucose time-series data comprises one or more of doses or amounts of previously injected or ingested pharmacon data. The glucose time-series data may be continuous or semi-continuous.

In some embodiments, the iteratively estimating ranges from the pharmacon being removed from 0 to the pharmacon having the full amount.

In some embodiments, outputting the XOB estimate comprises outputting the XOB estimate to at least one of a diabetes management system, a diabetes management algorithm, a user interface, a bolus calculator, or an artificial pancreas (AP) system.

In some embodiments, the XOB estimate comprises the equivalent amount of a pharmacon left in a subject. The pharmacon comprises at least one of insulin or carbohydrates.

In an embodiment, a system comprises an input compiler, wherein the input compiler receives and processes input data relating to a pharmacon; an exogenous pharmacon on board (XOB) estimator, wherein the XOB estimator uses estimation to account for transient changes in pharmacon absorption of the pharmacon, and wherein the XOB estimator determines an XOB estimation; and an output compiler, wherein the output compiler renders the XOB estimation.

In some embodiments, the transient changes in pharmacon absorption are determined by data from a continuous glucose monitoring (CGM) system. The XOB estimation may comprise an insulin on board (JOB) estimation and/or a carbohydrates on board (COB) estimation. The pharmacon may be insulin and/or carbohydrates.

In some embodiments, the input data corresponds to glucose concentration readings provided by a continuous glucose monitoring (CGM) system, insulin injection/infusion data, data on ingested meals, glucagon or other pharmacon dose and/or injection data, exercise data, or stress data. The input data may comprise data pertaining to insulin and/or data pertaining to carbohydrates.

In some embodiments, the system further comprises a continuous glucose monitoring (CGM) system in communication with the input compiler and configured to provide the input data to the input compiler. Alternatively or additionally, the system further comprises a closed-loop delivery system in communication with the input compiler and configured to provide the input data to the input compiler. The input data may comprise a sequence of insulin dose recommendations or glucagon dose recommendations.

In some embodiments, the input compiler is configured to compile at least one of (1) data related to a pharmacon whose glucose-effect equivalent is being compiled or (2) data related to the relevant history of continuous glucose monitoring (CGM) system readings.

In some embodiments, the XOB estimator is configured to estimate the glucose equivalent effect of the pharmacon at a predetermined time. The XOB estimator may comprise a baseline time-series estimator, an iterative time-series comparator, and a time-series comparator. The baseline time-series estimator may be a stateless machine that receives historical XOB amounts and continuous glucose monitoring (CGM) system history and produces a time-series that approximates future values of glucose. The iterative time-series comparator may be configured to combine a procedure that generates candidate XOB amounts with a modification of the time-series estimator in which historical XOB amounts are substituted with the XOB amount under consideration. The time-series comparator may be configured to match a pair of time-series that can be any measure of distance or similarity between the series.

In an embodiment, a method comprises receiving insulin data for a time T1, and continuous glucose monitoring (CGM) system time-series data for a time period preceding a time T2 of insulin on board (JOB) estimation; estimating baseline glucose time-series data from the time T2 of IOB estimation into a time T3 based on the insulin data for time T1 and CGM system data for the time period preceding T2; iteratively estimating a plurality of glucose time-series data from the time T2 to the time T3 based on a range of possible values for the insulin data at the time T2 and the CGM data for the time period preceding T2; comparing the baseline glucose time-series data with the plurality of glucose time-series to determine a best match from which an IOB estimate is selected; and outputting the IOB estimate.

In some embodiments, the insulin data is received from one of a subject or a connected device. The connected device may be an insulin pump.

In some embodiments, the method further comprises removing at least one of non-reliable data or spurious data from the insulin data and the CGM system time-series data. At least one of the insulin data or the CGM system time-series data comprises one or more of doses or amounts of previously injected or ingested insulin data. The CGM system time-series data may be continuous or semi-continuous.

In some embodiments, the iteratively estimating ranges from the insulin being removed from 0 to the insulin having the full amount.

In some embodiments, outputting the IOB estimate comprises outputting the IOB estimate to at least one of a diabetes management system, a diabetes management algorithm, a user interface, a bolus calculator, or an artificial pancreas (AP) system. The IOB estimate may comprise the equivalent amount of insulin left in a subject.

In an embodiment, a method comprises receiving carbohydrate data for a time T1, and continuous glucose monitoring (CGM) system time-series data for a time period preceding a time T2 of carbohydrates on board (COB) estimation; estimating baseline glucose time-series data from the time T2 of COB estimation into a time T3 based on the carbohydrate data for time T1 and CGM system data for the time period preceding T2; iteratively estimating a plurality of glucose time-series data from the time T2 to the time T3 based on a range of possible values for the carbohydrate data at the time T2 and the CGM data for the time period preceding T2; comparing the baseline glucose time-series data with the plurality of glucose time-series to determine a best match from which a COB estimate is selected; and outputting the COB estimate.

In some embodiments, the carbohydrate data is received from one of a subject or a connected device. The connected device may be a glucose monitor.

In some embodiments, the method further comprises removing at least one of non-reliable data or spurious data from the carbohydrate data and the CGM system time-series data. At least one of the carbohydrate data or the CGM system time-series data comprises one or more of doses or amounts of previously injected or ingested carbohydrate data. The CGM system time-series data may be continuous or semi-continuous.

In some embodiments, the iteratively estimating ranges from the carbohydrates being removed from 0 to the carbohydrates having the full amount.

In some embodiments, outputting the COB estimate comprises outputting the COB estimate to at least one of a diabetes management system, a diabetes management algorithm, a user interface, a bolus calculator, or an artificial pancreas (AP) system. The COB estimate may comprise the equivalent amount of carbohydrate left in a subject.

In an embodiment, a system comprises an automated insulin delivery (AID) algorithm configured to receive an estimate of a glucose concentration of a patient; and an insulin on board (JOB) estimator configured to provide an IOB estimate to the AID algorithm.

In some embodiments, the AID algorithm is comprised within a computing device. Alternatively or additionally, the AID algorithm comprises a semi closed-loop algorithm, a closed-loop algorithm, or an algorithmic recommendation system. The AID algorithm may be further configured to receive an updated estimate of the glucose concentration of the patient at predetermined intervals of time.

In some embodiments, the estimate of the glucose concentration of the patient is received as a continuous glucose monitoring (CGM) reading from a CGM sensor.

In some embodiments, the AID algorithm is configured to compute a desired insulin dose using the estimate of the glucose concentration of the patient. Alternatively or additionally, the AID algorithm is further configured to subtract the IOB estimate from the desired insulin dose to compute a bolus recommendation. Alternatively or additionally, the AID algorithm is further configured to provide the bolus recommendation to an insulin pump for delivering insulin to the patient.

In an embodiment, a method comprises receiving an estimate of a glucose concentration of a patient; receiving an insulin on board (JOB) estimate; computing a desired insulin dose using the estimate of the glucose concentration of the patient; and subtracting the IOB estimate from the desired insulin dose to compute a bolus recommendation In some embodiments, the method further comprises providing the bolus recommendation to an insulin pump for delivering insulin to the patient.

In some embodiments, the method further comprises receiving an updated estimate of the glucose concentration of the patient at predetermined intervals of time.

In some embodiments, the estimate of the glucose concentration of the patient is received as a continuous glucose monitoring (CGM) reading from a CGM sensor.

In an embodiment, a system comprises a monitoring device configured to receive input data pertaining to a patient; a handheld computing device configured to receive the input data from the monitoring device; and an exogenous pharmacon on board (XOB) calculator configured to perform an XOB estimation using the input data.

In some embodiments, the XOB calculator is locally implemented on a computing device. Alternatively, the XOB calculator is locally implemented on a computing device.

In some embodiments, the monitoring device comprises an insulin pen. The insulin pen may be configured to provide additional input data to the handheld computing device, wherein the XOB calculator is configured to perform the XOB estimation using the input data and the additional input data.

In some embodiments, the XOB calculator is further configured to render the XOB estimation via a display of the handheld computing device.

In some embodiments, the system further comprises an insulin pump configured to receive data from the handheld computing device and provide an amount of insulin to the patient based on the data received from the handheld computing device.

In some embodiments, the system further comprises an insulin pump configured to receive data from the handheld computing device and provide an amount of insulin to the patient based on the data received from the handheld computing device. Alternatively or additionally, the input data comprises data pertaining to insulin and/or the input data comprises data pertaining to carbohydrates.

In some embodiments, the XOB estimation comprises an insulin on board (JOB) estimation, and/or the XOB estimation comprises an insulin on board (JOB) estimation.

In some embodiments, the input data comprises a sequence of insulin dose recommendations or glucagon dose recommendations.

In some embodiments, the XOB calculator comprises an XOB estimator. The XOB estimator may be configured to estimate a glucose equivalent effect of a pharmacon at a predetermined time.

In some embodiments, the XOB estimator comprises a baseline time-series estimator, an iterative time-series comparator, and a time-series comparator. The baseline time-series estimator may be a stateless machine that receives historical XOB amounts and continuous glucose monitoring (CGM) system history and produces a time-series that approximates future values of glucose. The iterative time-series comparator may be configured to combine a procedure that generates candidate XOB amounts with a modification of the time-series estimator in which historical XOB amounts are substituted with the XOB amount under consideration. The time-series comparator may be configured to match a pair of time-series that can be any measure of distance or similarity between the series.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for managing diabetes comprising:
    receiving exogenous pharmacon data for a time T1, and glucose time-series data for a time period preceding a time T2 of on board estimation of the pharmacon;
    estimating baseline glucose time-series data from the time T2 of XOB estimation into a time T3 based on the data for time T1 and continuous glucose monitoring (CGM) system data for the time period preceding T2;
    iteratively estimating a plurality of glucose time-series data from the time T2 to the time T3 based on a range of possible values for the data at the time T2 and the CGM data for the time period preceding T2;
    comparing the baseline glucose time-series data with the plurality of glucose time-series to determine a best match from which an exogenous pharmacon on board (XOB) estimate is selected; and
    outputting the XOB estimate; and
    injecting or infusing an amount of insulin to a patient based on the XOB estimate for treatment of diabetes.

2. The method of claim 1, wherein the exogenous pharmacon data is received from one of a subject or a connected device.

3. The method of claim 2, wherein the connected device is an insulin pump.

4. The method of claim 1, wherein the exogenous pharmacon data comprises at least one of insulin on board (IOB) or carbohydrates on board (COB).

5. The method of claim 1, further comprising removing at least one of non-reliable data or spurious data from the exogenous pharmacon data and the glucose time-series data.

6. The method of claim 1, wherein at least one of the exogenous pharmacon data or the glucose time-series data comprises one or more of doses or amounts of previously injected or ingested pharmacon data.

7. The method of claim 1, wherein the glucose time-series data is continuous or semi-continuous.

8. The method of claim 1, wherein the iteratively estimating ranges from the pharmacon being removed from 0 to the pharmacon having the full amount.

9. The method of claim 1, wherein the XOB estimate comprises the equivalent amount of a pharmacon left in a subject, wherein the pharmacon comprises at least one of insulin or carbohydrates.

10. A method for managing diabetes comprising:
    receiving insulin data for a time T1, and continuous glucose monitoring (CGM) system time-series data for a time period preceding a time T2 of insulin on board (IOB) estimation;
    estimating baseline glucose time-series data from the time T2 of IOB estimation into a time T3 based on the insulin data for time T1 and CGM system data for the time period preceding T2;
    iteratively estimating a plurality of glucose time-series data from the time T2 to the time T3 based on a range of possible values for the insulin data at the time T2 and the CGM data for the time period preceding T2;
    comparing the baseline glucose time-series data with the plurality of glucose time-series to determine a best match from which an IOB estimate is selected; and
    outputting the IOB estimate; and
    injecting or infusing an amount of insulin to a patient based on the XOB estimate for treatment of diabetes.

11. The method of claim 10, wherein the insulin data is received from one of a subject or a connected device.

12. The method of claim 11, wherein the connected device is an insulin pump.

13. The method of claim 10, further comprising removing at least one of non-reliable data or spurious data from the insulin data and the CGM system time-series data.

14. The method of claim 10, wherein at least one of the insulin data or the CGM system time-series data comprises one or more of doses or amounts of previously injected or ingested insulin data.

15. The method of claim 10, wherein the CGM system time-series data is continuous or semi-continuous.

16. The method of claim 10, wherein the iteratively estimating ranges from the insulin being removed from 0 to the insulin having the full amount.

17. The method of claim 10, wherein the IOB estimate comprises the equivalent amount of insulin left in a subject.

18. A method for managing diabetes comprising:
    receiving carbohydrate data for a time T1, and continuous glucose monitoring (CGM) system time-series data for a time period preceding a time T2 of carbohydrates on board (COB) estimation;
    estimating baseline glucose time-series data from the time T2 of COB estimation into a time T3 based on the carbohydrate data for time T1 and CGM system data for the time period preceding T2;
    iteratively estimating a plurality of glucose time-series data from the time T2 to the time T3 based on a range of possible values for the carbohydrate data at the time T2 and the CGM data for the time period preceding T2;
    comparing the baseline glucose time-series data with the plurality of glucose time-series to determine a best match from which a COB estimate is selected; and outputting the COB estimate; and injecting or infusing an amount of insulin to a patient based on the COB estimate for treatment of diabetes.

19. The method of claim 18, wherein the carbohydrate data is received from one of a subject or a connected device.

20. The method of claim 19, wherein the connected device is a glucose monitor.

21. The method of claim 18, further comprising removing at least one of non-reliable data or spurious data from the carbohydrate data and the CGM system time-series data.

22. The method of claim 18, wherein at least one of the carbohydrate data or the CGM system time-series data comprises one or more of doses or amounts of previously injected or ingested carbohydrate data.

23. The method of claim 18, wherein the CGM system time-series data is continuous or semi-continuous.

24. The method of claim 18, wherein the iteratively estimating ranges from the carbohydrates being removed from 0 to the carbohydrates having the full amount.

25. The method of claim 18, wherein the COB estimate comprises the equivalent amount of carbohydrate left in a subject.

\* \* \* \* \*